United States Patent
Altel et al.

(10) Patent No.: US 10,526,343 B2
(45) Date of Patent: Jan. 7, 2020

(54) HETEROCYCLIC SYSTEMS AND PHARMACEUTICAL APPLICATIONS THEREOF

(71) Applicant: University of Sharjah, Sharjah (AE)

(72) Inventors: Taleb H. Altel, Sharjah (AE); Raafat A El-Awady, Sharjah (AE); Srinivasulu Vunnam, Sharjah (AE); Farah Ibrahim Al-Marzooq, Sharjah (AE)

(73) Assignee: UNIVERSITY OF SHARJAH (AE)

( * ) Notice: Subject to any disclaimer, the term of this patent is extended or adjusted under 35 U.S.C. 154(b) by 0 days.

(21) Appl. No.: 15/935,120

(22) Filed: Mar. 26, 2018

(65) Prior Publication Data

US 2019/0292202 A1 Sep. 26, 2019

(51) Int. Cl.
| | |
|---|---|
| C07D 498/14 | (2006.01) |
| C07D 513/22 | (2006.01) |
| A61K 31/429 | (2006.01) |
| A61K 31/4188 | (2006.01) |
| A61K 31/553 | (2006.01) |
| A61P 31/04 | (2006.01) |
| C07D 513/14 | (2006.01) |
| C12Q 1/18 | (2006.01) |

(52) U.S. Cl.
CPC ........ *C07D 498/14* (2013.01); *A61K 31/4188* (2013.01); *A61K 31/429* (2013.01); *A61K 31/553* (2013.01); *A61P 31/04* (2018.01); *C07D 513/14* (2013.01); *C07D 513/22* (2013.01); *C12Q 1/18* (2013.01)

(58) Field of Classification Search
CPC .. C07D 498/22; C07D 513/22; A61K 31/429; A61K 31/4188; A61K 31/553; A61P 31/04
USPC ....... 540/468, 469; 514/211.1; 544/468, 469
See application file for complete search history.

(56) References Cited

U.S. PATENT DOCUMENTS

| | | |
|---|---|---|
| 2,609,275 A | 9/1952 | Golding |
| 4,162,253 A | 7/1979 | Acheson et al. |
| 4,247,569 A | 1/1981 | Hata et al. |
| 6,911,525 B2 | 6/2005 | Hill et al. |
| 6,946,458 B2 | 9/2005 | Turos |
| 6,989,447 B2 | 1/2006 | Markwell et al. |
| 7,176,214 B2 | 2/2007 | Pitts et al. |
| 7,232,832 B2 | 6/2007 | Axten et al. |
| 7,390,806 B2 | 6/2008 | Lee et al. |
| 7,709,472 B2 | 5/2010 | Miller et al. |
| 8,058,425 B2 | 11/2011 | Engler et al. |
| 8,415,347 B2 | 4/2013 | Cid-Núñez et al. |
| 8,691,859 B2 | 4/2014 | Bavari et al. |
| 8,809,333 B2 | 8/2014 | Brown et al. |
| 8,916,542 B2 | 12/2014 | Baker et al. |
| 9,517,994 B2 | 12/2016 | Ebright et al. |
| 2008/0234294 A1 | 9/2008 | Kovarik et al. |
| 2011/0257078 A1 | 10/2011 | Young et al. |

FOREIGN PATENT DOCUMENTS

| | | |
|---|---|---|
| WO | 2004058144 A2 | 7/2004 |
| WO | 2009080788 A2 | 7/2009 |
| WO | 2010075215 A1 | 7/2010 |
| WO | 2012051663 A1 | 4/2012 |
| WO | 2017098257 A1 | 6/2017 |
| WO | 2017125944 A1 | 7/2017 |

OTHER PUBLICATIONS

Theuretzbacher et al. Current Opinion in Pharmacology, 2011, 11: 429-432.*
Bassetti et al. Annals of Clinical Microbiology and Antimicrobials 2013, 12:22, pp. 1-15.*
Shaffer R. K. Yale Journal of Biology and Medicine 86 (2013), pp. 261-270.*
Kint et al. Trends in Microbiology, Dec. 2012, vol. 20, No. 12, 577-585.*
Becker D.E. Anesth Prog 60:111-123, 2013.*
Singh S.B., Bioorganic & Medicinal Chemistry Letters 24 (2014) 3683-3689.*
Wilson D.N.,Critical Reviews in Biochemistry and Molecular Biology, 2009;44(6): 393-433.*
Maguire B.A., Microbiology and Molecular Biology Reviews, Mar. 2009, p. 22-35.*
Rehm et al.,Clinical Infectious Diseases 2010; 51 (2):176-182.*
Babic et al., Drug Resistance Updates 9, 142-156, 2006.*
Paterson et al., Clinical Microbiological reviews 18(40, 657-686, 2005.*
Wolff Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
Sarhan et al., "Cell cycle disruption and apoptotic activity of 3-aminothiazolo[3,2-a]benzimidazole-2-carbonitrile and its homologues", European Journal of Medicinal Chemistry, vol. 45, Issue 6, Jun. 2010, pp. 2689-2694, 1 page (Abstract Only).
Almansour et al., "Synthesis, Spectroscopic, X-ray Diffraction and DFT Studies of Novel Benzimidazole Fused-1,4-Oxazepines", Molecules, MDPI, vol. 21, Issue 6, 2016, 15 pages.
Castanedo et al., "Structure-Based Design of Tricyclic NF-κB Inducing Kinase (NIK) Inhibitors That Have High Selectivity over Phosphoinositide-3-kinase (PI3K)", Journal of Medicinal Chemistry, American Chemical Society, vol. 60, Issue 2, pp. 627-640, 2016, 1 page (Abstract only).

(Continued)

*Primary Examiner* — Venkataraman Balasubramanian
(74) *Attorney, Agent, or Firm* — Hayes Soloway PC

(57) ABSTRACT

Novel heterocyclic fused systems are disclosed herein which possess numerous biological activities, including but not limited to antibacterial activity, and usefulness to the treatment of many disease states, such as pathogenic infections. In particular, new imidazoles are disclosed along with related processes of preparation and methods of use as antibacterial agents. The disclosed compounds were found to be active against several Gram-positive bacteria, including *Enterococcus faecalis* and *Bacillus subtilis*, and were also found to be active against several species of multi-drug resistant *Staphylococcus*, such as *S. aureus, S. saprophyticus, S. haemolyticus*, and *S. epidermidis*.

12 Claims, 4 Drawing Sheets

(56) References Cited

OTHER PUBLICATIONS

Toner et al., "Antimicrobial Resistance Is a Global Health Emergency", Health Security, vol. 13, No. 3, 2015, pp. 153-155, 3 pages.
U.S. Department of Health and Services, Center for Disease Control and Prevention, "Antibiotic Use in the United States, Progress and Opportunities", 2017, 40 pages.
O'Neill, "Tackling Drug-Resistant Infections Globally: Final Report and Recommendations", 2016, 84 pages.
World Health Organization, "Antimicrobial Resistance, Key Facts", Feb. 15, 2018, http://www.who.int./en/news-room/fact-sheets/detail/antimicrobial-resistance, 9 pages.
Welsch et al., "Privileged Scaffolds for Library Design and Drug Discovery", Curr Opin Chem Biol Jun. 2010, vol. 14, Issue 3, pp. 347-361, 20 pages.
Koh et al., "Phenotypic screening to identify small-molecule enhancers for glucose uptake: target identification and rational optimization of their efficacy", US National Library of Medicine National Institutes of Health, Angew. Chem. Int. Ed. Engl., vol. 53, Issue 20, p. 5102, 1 page (Abstract Only).
Lee et al., "Systems metabolic engineering of microorganisms for natural and non-natural chemicals", US National Library of Medicine National Institutes of Health, Nat. Chem. Biol., vol. 8, Issue 6, pp. 536-46, May 17, 2012, 1 page (Abstract Only).
Al-Tel et al., "Modular Bi-Directional One-Pot Strategies for the Diastereoselective Synthesis of Structurally Diverse Collections of Constrained β-Carboline-Benzoxazepines", Chemistry A European Journal, Oct. 12, 2017, vol. 23, pp. 14182-14192, 2 pages (Abstract Only).
Al-Tel et al., "Intramolecular Diaza-Diels_Alder Protocol: A New Diastereoselective and Modular One-Step Synthesis of Constrained Polycyclic Frameworks", Chemistry A European Journal, 2016, pp. 4137-4148, 1 page (Abstract Only).
"Performance Standards for Antimicrobial Disk Susceptibility Testing", Clinical and Laboratory Standards Institute CLSI, Jan. 2012, M02-A11, vol. 32, No. 1, 23 pages.
"Performance Standards for Antimicrobial Disk Susceptibility Testing", Clinical and Laboratory Standards Institute CLSI, Jan. 2016, M100S, 26th Edition, M02-A11, vol. 326 No. 1, 256 pages.
Dufrene, "Atomic Force Microscopy, a Powerful Tool in Microbiology", Journal of Bacteriology, Oct. 2002, pp. vol. 184, Issue No. 19, pp. 5205-5213, 9 pages.
Dufrene, "Atomic Force Microscopy in Microbiology: New Structural and Functional Insights into the Microbial Cell Surface", mBio, Jul./Aug. 2014, vol. 5, Issue 4, 14 pages.
Cochrane et al., "Antimicrobial lipopeptide tridecaptain A1 selectively binds to Gram-negative lipid II", PNAS, Oct. 2016, vol. 113, Issue No. 41, pp. 11561-11566, 6 pages.
Lopez-Jimenez et al., "Atomic force microscopy visualization of injuries in Enterococcus faecalis surface caused by ER,CrYSGG and diode lasers", Med Oral Patol Cir Bucal, Jan. 2015, vol. 20, Issue 1, pp. 45-51, 7 pages.
Vichai et al., "Sulforhodamine B colorimetric assay for cytotoxicity screening", Nature Protocols, Aug. 17, 2006, vol. 1, Issue No. 3, pp. 1112-1116, 5 pages.
Eloff, "Methods for Dilution Antimicromial Susceptibility Tests for Bacteria that Grow Aerobically", Clinical and Laboratory Standard Institute, Jan. 2015, M07-A10, vol. 35, Issue No. 2, 110 pages.
Balouiri et al., "Methods for in vitro evaluating antimicrobial activity: A review", Journal of Pharmaceutical Analysis, Jun. 2016, pp. 71-79, 9 pages.
Foerster et al., "Time-kill curve analysis and pharmacodynamic modelling for in vitro evaluation of antimicrobials against Neisseria gonorrhoeae", BMC Microbiology, 2016, vol. 16, 11 pages.
Soon et al., "Atomic Force Microscopy Investigation of the Morphology and Topography of Colistin-Heteroresistant Acinetobacter baumannii Strains as a Function of Growth Phase and in Response Colistin Treatment", American Society for Microbiology, Antimicrobial Agents and Chemotherapy, Dec. 2009, vol. 53, Issue No. 12, pp. 4979-4986, 8 pages.
Khalifa et al., "Resazurin Microtiter Assay Plate method for detection of susceptibility of multidrug resistant *Mycobacterium tuberculosis* to second-line anti-tuberculous drugs", Egyptian Journal of Chest Diseases and Tuberculosis, 2013, vol. 62, pp. 241-247, 7 pages.
Palomino et al., "Resazurin Microtiter Assay Plate: Simple and Inexpensive Method for Detection of Drug Resistance in *Mycobacterium tuberculosis*", Antimicrobial Agents and Chemotherapy, Aug. 2002, vol. 46, Issue 8, pp. 2720-2722, 3 pages.
Taneja et al., "Resazurin reduction assays for screening of antitubercular compounds against dormant and actively growing *Mycobacterium tuberculosis, Mycobacterium bovis* BCG and *Mycobacterium smegmatis*", Journal of Antimicrobial Chemotherapy, 2007, vol. 60, pp. 288-293, 6 pages.
Bopp et al., "Comparison of four different colorimetric and fluorometric cytotoxicity assays in a zebrafish liver cell line", BMC Pharmacology, BioMed Central, May 30, 2008, 11 pages.
Ridgway et al., "Clinical Significance of Methicillin-Resistant *Staphylococcus aureus* Colonization on Hospital Admission: One-Year Infection Risk", PLOS|one, 2013, 8(11): e79716. doi:10.1371, 9 pages.
Wilderstrom, "Significance of *Staphylococcus epidermidis* in Health Care-Associated Infections, from Contaminant to Clinically Relevant Pathogen: This is a Wake-Up Call!", Journal of Clinical Microbiology, American Society for Microbiology, Jul. 2016, vol. 54, Issue No. 7, pp. 1679-1681, 3 pages.

* cited by examiner

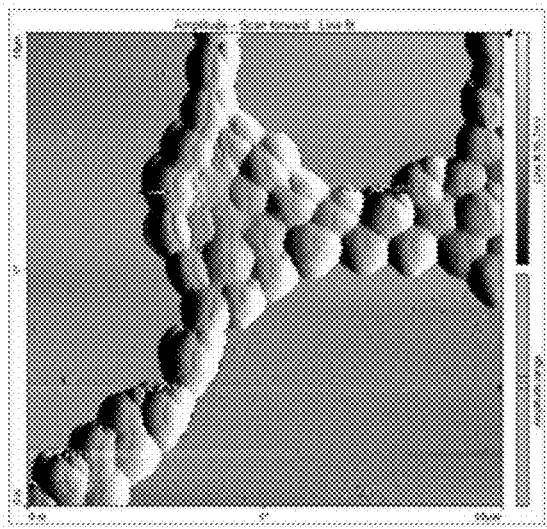
FIG. 5A1
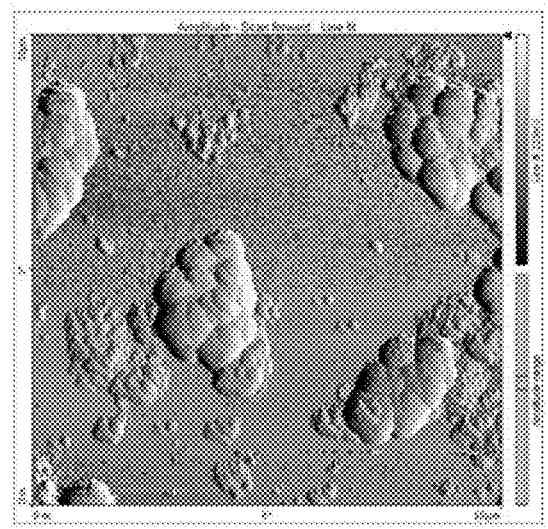
FIG. 5A2
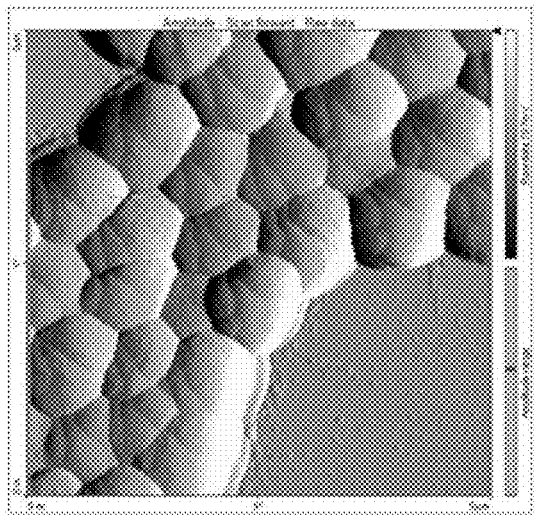
FIG. 5B1
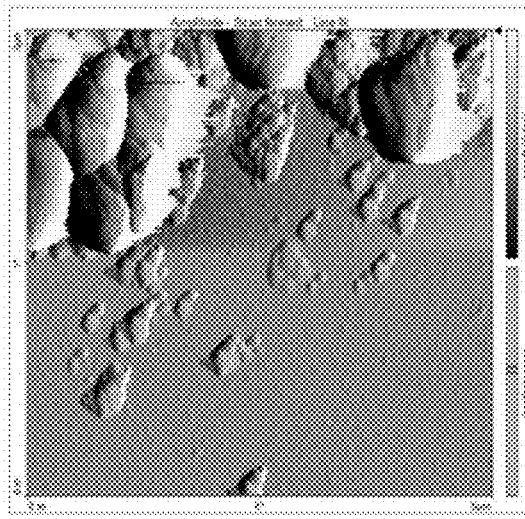
FIG. 5B2

HETEROCYCLIC SYSTEMS AND PHARMACEUTICAL APPLICATIONS THEREOF

FIELD OF THE INVENTION

The present disclosure relates to novel imidazole fused polycyclic systems, methods for their use, and processes for their preparation. The compounds of the present disclosure are particularly useful against a variety of bacteria, including multidrug resistant strains of *Staphylococcus aureus, S. saprophyticus, S. haemolyticus*, and *S. epidermidis*.

BACKGROUND

Antibacterial resistance is a global clinical and public health problem that has emerged with alarming rapidity in recent years and, undoubtedly, will increase in the near future. According to the statistics of the Center for Disease Control and Prevention (CDC), infections with antibiotic-resistant bacteria cause more than 2 million illnesses and about 23,000 deaths each year in the United States. Recent research estimates that by 2050, 10 million people may die annually due to infections caused by antibiotic-resistant bacteria. Moreover, mortality due to infection is soon expected to be more than that caused by cancer. Antibiotic resistance will also have a cumulative cost of at least 100 trillion USD, more than one and a half times the annual world Gross Domestic Product (GDP) today. In the United States, there are about 47 million unnecessary antibiotic prescriptions issued each year. These unnecessary prescriptions are made to conditions that do not require antibiotics, such as viral infections which do not respond to antibiotics. Excessive use of antibiotics over the past few decades has led to the development of bacteria that is resistant to currently available antibiotics. Most newly developed antimicrobials are chemical variants of older agents; therefore, resistance can develop quickly. Indeed, bacterial strains resistant to many existing antibiotics are continually being isolated and there is an urgent need to identify new antimicrobial agents with improved activity against both Gram-positive and Gram-negative organisms.

*Staphylococcus* is one of most clinically important species of Gram-positive bacteria and methicillin-resistant *Staphylococcus aureus* (MRSA) causes many severe infections. The World Health Organization has included this bacterium in its list of the top 12 pathogens causing high morbidity and mortality worldwide. Due to the limited therapeutic options currently available to combat this bacterium, patients infected with MRSA are estimated to have 64% more mortality risk than patients infected with other non-resistant forms of the bacteria.

SUMMARY

The present invention relates to novel imidazole fused polycyclic systems, methods for their use, and processes for their preparation. The presently disclosed compounds are particularly useful against a variety of bacteria, including multidrug resistant strains of *Staphylococcus aureus, S. saprophyticus, S. haemolyticus*, and *S. epidermidis*. The presently disclosed compounds are more likely to be useful as antibacterial agents as they have potent activity on a variety of multidrug resistant bacteria, including both clinical and environmental isolates. Additionally, as the disclosed compounds are embedded within biologically active ring systems, their applications to serve as pharmaceutical agents to treat different diseases are extendable.

Phenotype-based screening of diverse compound collections generated by privileged substructure-based diversity-oriented synthesis (pDOS) is considered one of the prominent approaches in the discovery of novel drug leads. Indeed, pDOS is a very attractive technique to synthesize small molecule collections with chemical scaffolds that frequently exist in natural products as well as drugs that can target previously unexploited features of disease-relevant proteins. While oxazapine, diazapine, imidazole, and thiazole skeletons and analogs constitute the core scaffold of many bioactive natural products and synthetic drugs, a key challenge is the development of efficient and modular synthetic routes toward small-molecule libraries of compounds with skeletal and stereochemical complexity as well as drug-like properties.

As part of the global effort to fight antibiotic-resistant pathogens, a new series of novel imidazole fused polycyclic compounds is disclosed herein along with demonstrated potent antibacterial activity against several Gram-positive resistant bacteria. In particular, the presently disclosed novel imidazole fused polycyclic compounds have a general formula A, as shown below.

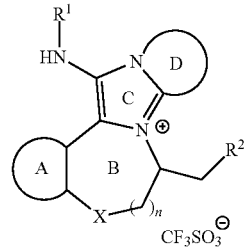

General formula A

In general formula A:

denotes a 5, 6, or 7 membered aryl, heteroaryl, alicyclic, or heteroalicyclic ring which may be unsubstituted or substituted with 1, 2, 3, or 4 substituents independently selected from the group consisting of: a halogen atom, CN, $R^3$, $OR^3$, $SR^3$, $N(R^3)_2$, $C(O)R^3$, $C(O)OR^3$, $NR^3C(O)R^3$, $C(O)NR^3$, $SO_2R^3$, $NR^3SO_2R^3$, and $SO_2N(R^3)_2$;

X denotes —O, —$NR^1$, —$NSO_2R^1$, —$CH_2$, —$CHR^1$, or —$C(R^1)_2$;

n=1, 2, or 3, which provides ring B with 7, 8, or 9 members, respectively;

denotes a 5, 6, or 7 membered aryl or heteroaryl ring which may be unsubstituted or substituted with 1, 2, 3, or 4 substituents independently selected from the group consisting of: a halogen atom, CN, $R^3$, $OR^3$, $SR^3$, $N(R^3)_2$, $C(O)R^3$, $C(O)OR^3$, $NR^3C(O)R^3$, $C(O)NR^3$, $SO_2R^3$, $NR^3SO_2R^3$, and $SO_2N(R^3)_2$;

$R^1$ is hydrogen or an unsubstituted or substituted alkyl, aryl, or heteroaryl group;

$R^2$ is selected from the group consisting of: $C(O)OR^3$, CN, $N(R^3)_2$, $C(O)R^3$, $C(O)NR^3$, $SO_2R^3$, $SO_2N(R^3)_2$, and $PO_2R^3$; and $R^3$ is independently hydrogen or a substituted group selected from the group consisting of: an alkyl group; a monocyclic 3-8 membered saturated, partially unsaturated, or aryl ring having 0-4 heteroatoms independently selected from nitrogen, oxygen, or sulfur; and a bicyclic 8-10 membered saturated, partially unsaturated, or aryl ring having 0-5 heteroatoms independently selected from nitrogen, oxygen, or sulfur.

In addition to compounds having the general formula A, enantiomers, diastereoisomers, racemates, pharmaceutically acceptable salts thereof are also within the scope of the present disclosure.

In another embodiment, the present disclosure also provides novel compounds of a general formula B, having the following general chemical formula:

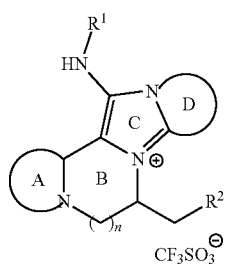

General formula B

In general formula B:

denotes a 5, 6, or 7 membered heteroaryl or heteroalicyclic ring which may be unsubstituted or substituted with 1, 2, 3, or 4 substituents independently selected from the group consisting of: a halogen atom, CN, $R^3$, $OR^3$, $SR^3$, $N(R^3)_2$, $C(O)R^3$, $C(O)OR^3$, $NR^3C(O)R^3$, $C(O)NR^3$, $SO_2R^3$, $NR^3SO_2R^3$, and $SO_2N(R^3)_2$;

n=1, 2, or 3 which provides ring B with 6, 7, or 8 members, respectively;

denotes a 5, 6, or 7 membered heterocyclic ring which may be unsubstituted or substituted with 1, 2, 3, or 4 substituents independently selected from the group consisting of: a halogen atom, CN, $R^3$, $OR^3$, $SR^3$, $N(R^3)_2$, $C(O)R^3$, $C(O)OR^3$, $NR^3C(O)R^3$, $C(O)NR^3$, $SO_2R^3$, $NR^3SO_2R^3$, and $SO_2N(R^3)_2$;

$R^1$ is hydrogen or an unsubstituted or substituted alkyl, aryl, or heteroaryl group;

$R^2$ is selected from the group consisting of: $C(O)OR^3$, CN, $N(R^3)_2$, $C(O)R^3$, $C(O)NR^3$, $SO_2R^3$, $SO_2N(R^3)_2$, and $PO_2R^3$; and $R^3$ is independently hydrogen or a substituted group selected from the group consisting of: a $C_{1-6}$ aliphatic group; a monocyclic 3-8 membered saturated, partially unsaturated, or aryl ring having 0-4 heteroatoms independently selected from nitrogen, oxygen, or sulfur; and a bicyclic 8-10 membered saturated, partially unsaturated, or aryl ring having 0-5 heteroatoms independently selected from nitrogen, oxygen, or sulfur.

In addition to compounds having the general formula B, the present disclosure is also intended to include enantiomers, diastereoisomers, racemates, and pharmaceutically acceptable salts thereof.

Compounds of general formula A can be prepared by any suitable method. For example, in some embodiments, a one-pot reaction between compounds of general formulas I, II and III (illustrated below) provides compounds of the general formula A via Groebke and aza-Michael reactions.

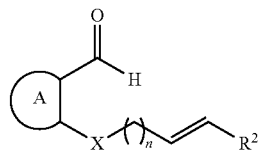

General formula I

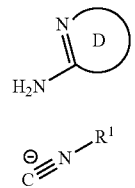

General formula II

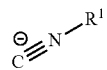

General formula III

In general formulas I, II, and III,

,

X,

, n, $R^1$, and $R^2$ are as previously described herein.

Compounds of the general formula B may be prepared by any suitable technique. In some embodiments, a one-pot reaction between compounds of general formulas IV, II, and III (illustrated below) can be used to provide the novel compounds of general formula B via Groebke and aza-Michael reactions.

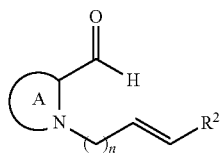

General formula IV

General formula II

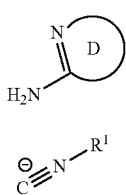

General formula III

In general formula IV,

X,

n, $R^1$, and $R^2$ are as previously described herein.

In another aspect, the present disclosure also provides pharmaceutical compositions comprising compounds of the general formulas A and/or B.

In yet another aspect, the subject disclosure provides methods of use of the compounds of general formulas A and/or B to treat bacterial infections.

BRIEF DESCRIPTION OF THE DRAWINGS

FIG. 5A1 shows an image obtained with atomic force microscopy (AFM) of an untreated MRSA-1 strain obtained at a scan size of 10 μm².

FIG. 5B1 shows an AFM image of an untreated MRSA-1 strain obtained at a scan size of 5 μm².

FIG. 5A2 shows an AFM image of a MRSA-1 strain treated with compound 1o obtained at a scan size of 10 μm².

FIG. 5B2 shows an AFM image of a MRSA-1 strain treated with compound 1o obtained at a scan size of 5 μm².

DETAILED DESCRIPTION

Figure 1:
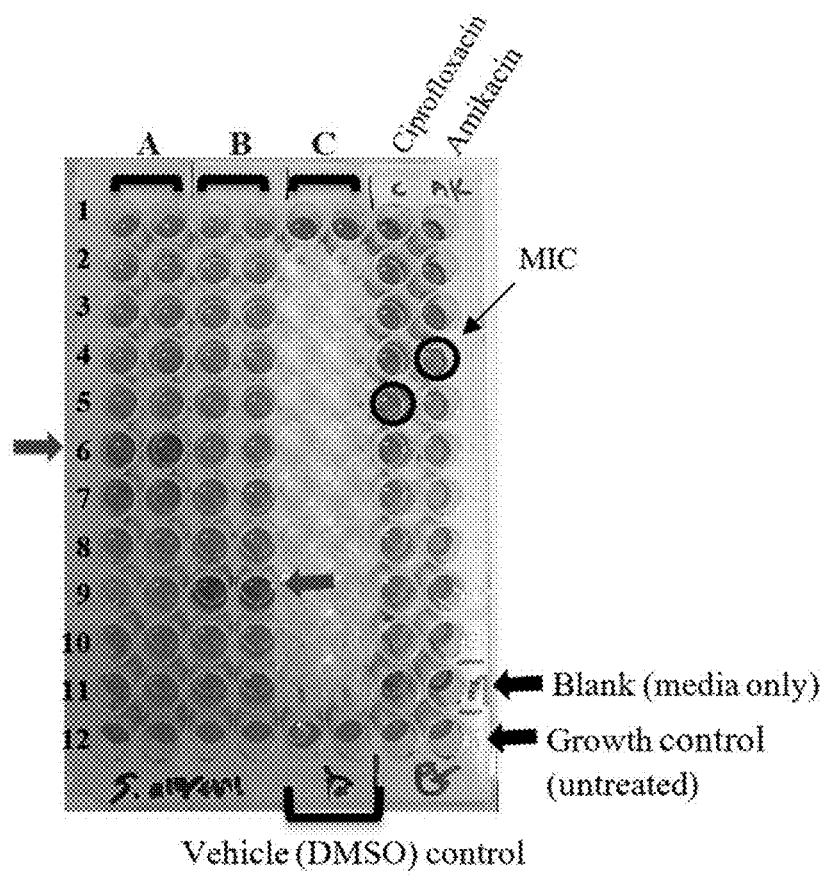
FIG. 1 shows a photograph of a cell viability assay conducted to screen the disclosed compounds for potential antibacterial activities, in accordance with some embodiments of the subject disclosure.

The subject disclosure provides novel imidazole fused polycyclic ring systems of the general formulas A and B, methods of preparing these systems, and uses of such novel compounds for different disease states, including as treatment agents for pathogenic infections. When discussing the disclosed compounds and compositions, the following terms have the following meaning unless otherwise indicated.

The term "aryl" means an aromatic or partially aromatic hydrocarbon group containing 6 to 10 carbon atoms and consisting of one or two rings which may be fused to each other or attached to each other via a single bond. Examples of aryl groups are phenyl, napthyl, biphenyl, and indenyl.

The term "heteroaryl," as used herein, means an aromatic or partially aromatic group consisting of one or two rings, which may be fused to each other or attached to each other via a single bond. A ring of a heteroaryl group may contain 5 to 10 ring atoms wherein up to four (e.g., one, two, three, or four) ring atoms are heteroatom(s) and the remaining ring atoms are carbon. Examples of heteroaryl groups include, but are not limited to: pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

The term "alicyclic" means a saturated or unsaturated aliphatic cyclic ring system consisting of one or more rings, which may be fused to each other or attached to each other via a single bond. A ring of an alicyclic group may contain 5 to 10 atoms (e.g., carbon). Examples of alicyclic groups include cyclopentane, cyclohexane, cycloheptane, cyclooctane, and terpene.

The term "heteroalicyclic" means any five to seven membered monocyclic, saturated, or partially unsaturated ring structure containing at least one heteroatom selected from the group consisting of O, N, and S, and optionally containing one, two, or three additional heteroatoms independently selected from the group consisting of O, N, and S. In some embodiments, the term heteroalicyclic refers to a nine to ten membered saturated, partially unsaturated, partially aromatic bicyclic, or spiro-fused ring system containing at least one heteroatom selected from the group consisting of O, N, and S, and optionally containing one to four additional heteroatoms independently selected from the group consisting of O, N, and S. Examples of suitable heteroalicyclic groups include, but are not limited to: pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, 2-aza-spiro[4.5]decyl, and the like. A heterocycloalkyl group may be attached at any heteroatom or carbon atom of a heteroalicyclic ring, in some embodiments.

The term "alkyl," as used herein, denotes a saturated, linear, or branched chain hydrocarbon group containing 1 to 8 (e.g., 1 to 6 or 1 to 4) carbon atoms. For example, methyl, ethyl, propyl, isopropyl, 1-butyl, 2-butyl, and tert-butyl groups are alkyl groups. In select embodiments, "C1-C8 alkyl" groups have 1, 2, or 3 carbon atoms.

The term "halogen" means fluorine, chlorine, bromine, or iodine.

The term "substituted" means a group which may be substituted one to three times by a halogen atom, CN, $R^3$, $OR^3$, $SR^3$, $N(R^3)_2$, $C(O)R^3$, $C(O)OR^3$, $NR^3C(O)R^3$, $C(O)NR^3$, $SO_2R^3$, $NR^3SO_2R^3$, and/or $SO_2N(R^3)_2$. With reference to substituents, the term "independently" means that when more than one of such substituents is possible, such substituents may be the same or different from one another.

The term "pharmaceutically acceptable salt" refers to conventional acid-addition salts or base-addition salts that retain the biological effectiveness and properties of the compounds of the underlying chemical formula and are formed from suitable non-toxic organic or inorganic acids or organic or inorganic bases. Acid-addition salts include, for example, those derived from inorganic acids, such as hydrochloric acid, hydrobromic acid, hydroiodic acid, sulfuric acid, sulfonic acid, phosphoric acid, and nitric acid, and those derived from organic acids, such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and quaternary ammonium hydroxides, such as for example, tetramethyl ammonium hydroxide.

The term "polar-protic solvent" means a polar solvent which contains acidic hydrogen and acts as a hydrogen bond donor. Examples of polar-protic solvents include methanol, ethanol, and isopropanol.

The term "polar-aprotic solvent" means a polar solvent which does not contain acidic hydrogen and does not act as a hydrogen bond donor. Examples of polar-aprotic solvents are dimethylsulfoxide, dimethylformamide, hexamethylphosphorotriamide, n-methyl pyrrolidone, tetrahydrofuran, and acetonitrile (ACN).

The disclosed compounds may possess one or more asymmetric carbon atoms and are thus capable of existing in the form of optical isomers as well as in the form of racemic or non-racemic mixtures thereof. In some embodiments, the disclosed compounds may be utilized as a single isomer or as a mixture of stereochemical isomers. In embodiments in which diastereoisomers, i.e., nonsuperimposable stereochemical isomers, are used the diastereoisomers can be separated by any known technique, such as chromatography, distillation, crystallization, and/or sublimation. Optical isomers can be obtained by resolution of the racemic mixtures according to conventional processes, for example, by formation of diastereoisomeric salts by treatment with an optically active acid or base. Examples of appropriate acids that may be used, without limitation, tartaric, diacetyltartaric, dibenzoyltartaric, ditoluoyltartaric, and/or camphorsulfonic acid. A mixture of diastereomers can be separated by crystallization followed by liberation of optically active bases from these salts. An alternative process for separation of optical isomers includes the use of a chiral chromatography column, which may be chosen to maximize separation of the enantiomers.

In some embodiments, the disclosed compounds may be introduced to a patient in pro-drug form (i.e., as a biologically inactive compound that is metabolized in the body to produce a biologically active compound). In some such embodiments, the disclosed pro-drugs include a compound of formulas A and/or B and at least one pharmacologically acceptable protecting group which is removed under physiological conditions. Any suitable pharmacologically acceptable protecting group may be used, such as, for example, an alkoxy-, aralkyloxy-, acyl-, and/or acyloxy group (e.g., an ethoxy, benzyloxy, acetyl, or acetyloxy group).

The present disclosure also relates to the use of one or more of the disclosed compounds (at times referred to herein as "active ingredients") in the preparation of medicaments. In some embodiments, compounds of the formulas A and/or B are administered either individually or in combination with any other desired therapeutic agent, using suitable delivery methods. The disclosed therapeutically useful agents may be administered, for example, by one of the following routes: orally, for example in the form of dragees, coated tablets, pills, semi-solid substances, soft or hard capsules, solutions, emulsions or suspensions; parenterally, for example, in the form of an injectable solution; rectally in the form of suppositories; by inhalation, for example, in the form of a powder formulation or a spray; and/or transdermally or intranasally. For the preparation of such tablets, pills, semi-solid substances, coated tablets, dragees and hard gelatin capsules, the therapeutically usable product may be mixed with pharmacologically inert, inorganic or organic pharmaceutical carrier substances, for example, with lactose, sucrose, glucose, gelatin, malt, silica gel, starch or derivatives thereof, talcum, stearic acid or salts thereof, skimmed milk powder, and the like. For the preparation of soft capsules, pharmaceutical carrier substances such as, for example, vegetable oils, petroleum, animal or synthetic oils, wax, fat, and polyols may be used. For the preparation of liquid solutions and syrups, pharmaceutical carrier substances such as, for example, water, alcohols, aqueous saline solution, aqueous dextrose, polyols, glycerol, vegetable oils, petroleum, and animal or synthetic oils maybe used. For suppositories, pharmaceutical carrier substances such as, for example, vegetable oils, petroleum, animal or synthetic oils, wax, fat, and polyols may be used. For aerosol formulations, compressed gases that are suitable for this purpose, such as, for example, oxygen, nitrogen and carbon dioxide may be used. The pharmaceutically acceptable agents may also comprise additives for preserving and stabilizing, emulsifiers, sweeteners, flavor rings, salts for altering the osmotic pressure, buffers, encapsulation additives and/or antioxidants. Numerous configurations and variations will be apparent to those skilled in the art upon consideration of the subject disclosure.

As used herein, the following abbreviations and terms have the definitions provided below, unless otherwise stated.

The term "MIC" means a minimum inhibitory concentration, which is the lowest concentration of a chemical which is required to inhibit visible microbial growth following overnight incubation, usually reported in units of µg/mL.

The term "MBC" refers to a minimum bactericidal concentration, which is the lowest concentration of a chemical causing microbial death as indicated by absence of growth after subculture on antibiotic-free media.

The term "CFU" refers to a colony-forming unit, which is a unit used to estimate the number of viable microbial cells in a sample.

The term "resistant" or "resistance" to a bacterium or of a bacterial infection to an antibiotic includes a complete resistance to the antibiotic or a partial resistance which is defined herein as a circumstance in which the MIC of an antibiotic toward the organism in question has increased.

ACN=Acetonitrile
TFA=Trifluroacetic acid
EtOAc=Ethylacetate
DCM=Dicholoromethane
MeOH=Methanol
NMR=Nuclear magnetic resonance
HRMS=High resolution mass spectroscopy
LCMS=Liquid chromatography-mass spectroscopy
ESI-TOF=Electrosprayionization-time of flight The presently disclosed compounds exhibited broad antibacterial selectivity against multiple Gram-positive bacteria including *Staphylococcus aureus, Enterococcus faecalis*, and *Bacillus subtilis*. Additionally, the disclosed compounds also exhibited potent activity against multiple species of multidrug resistant *Staphylococcus*, including *S. aureus, S. saprophyticus, S. haemolyticus,* and *S. epidermidis*. Due to the powerful antibacterial properties exhibited, the presently disclosed compounds may also be used for any other medical applications, including as supplement feed for animals.

The presently disclosed compounds may also be used as medicaments or as substances for preserving inorganic and/or organic materials, such as polymers, lubricants, paints, fibers, leather, paper, timber, food stuffs, and/or water. In select embodiments in which the disclosed compounds are used in connection with a polymeric material, the compound(s) present may be covalently bonded to the polymeric material.

The presently disclosed compounds may also be used for the sterilization or disinfection of surfaces possibly contaminated with bacteria, for example, in hospitals, clinics, or in domestic settings. In select embodiments, the disclosed compounds may be used to sterilize medical equipment.

The disclosed compounds may also be used to prevent, alleviate, and/or cure diseases caused by pathogens whose growth is inhibited by these compounds. As explained in detail herein, the instant compounds are particularly active against bacteria and bacteria-like microorganisms. The presently disclosed compounds are thus suitable for use in human and veterinary medicine, for example, for prophylaxis and/or chemotherapy of local and systemic infections caused by these pathogens.

An illustrative (but not exhaustive) list of pathogenic microorganisms that may be possible targets of the presently disclosed compounds is as follows: Gram-positive bacteria Micrococcaceae, such as Staphylococci, for example, *Staphylococcus aureus, Staphylococcus epidermidis,* and *Staphylococcus aerogenes*; Lactobacteriaceae, such as Streptococci, for example, *Streptococcus pyogenes, Streptococcus pneumoniae,* and *Streptococcus mutans*; Bacillaceae, for example, *Bacillus subtilis, Bacillus anthracis* and *Bacillus cereus*; Corynebacteria, for example, *C. diptheriae, C. pseudotuberculosis,* and *C. ulcerans*; Clostridia bacteria, for example, *Clostridium difficile, Clostridium botulinum,* and *Clostridium perfringens*; and *Listeria* bacteria such as *Listeria monocytogenes*. Fungi, viruses, and parasites (e.g., malaria) are also possible targets for the disclosed compounds.

The disclosed compounds may, in some cases, be used to prevent, alleviate, and/or cure various diseases, such as: diseases of the respiratory passages and of the pharyngeal cavity; otitis; pharyngitis; pneumonia; bronchitis; peritonitis; pyelonephritis; cystitis; endocarditis; gastroenteritis; skin infections; and/or blood stream infections.

The presently disclosed compounds may, in some embodiments, be formulated as pharmaceutical compositions and administered to a patient, such as a human patient, in a variety of forms adapted to the chosen route of administration, i.e., orally or parenterally, by intravenous, intra muscular, topical, and/or subcutaneous routes. In some embodiments, the disclosed antibacterial compounds may be administrated in combination with known antibiotics, including those with a different mechanism of action.

The present disclosure provides novel imidazole fused polycyclic ring systems of the general formulas A and B along with methods of preparing these systems and uses for many disease states, including as antibacterial agents. The following experimental examples are included to provide further detail and are in no way intended to limit the scope of the present disclosure.

Example 1

In a first experimental example, novel compounds of the general formula A were prepared and characterized. The methods used to prepare these compounds and the resulting characterization data are provided below.

Aldehyde (general formula I, 0.5 mmol), 2-aminoazine (general formula II, 0.5 mmol), scandium triflate (20 mol %) and sodium sulfate (1.0 mmol) were mixed in ACN (2 mL) at room temperature. After 45 mins, isocyanide (general formula III, 0.55 mmol) was introduced and stirring was continued at room temperature for 12-15 hours. After completion of step-1 (Groebuk reaction), ytterbium triflate was added (30 mol %) and continued the reaction at 70° C. for 3 to 12 hours. After completion of step-2 (Michael reaction), ACN was removed and the obtained crude material was purified on flash column chromatography using a gradient of EtOAC/hexane or MeOH/DCM as mobile phase eluents to obtain pure products of general formula A.

Compound 1a had the following chemical formula and characterization data:

Compound 1a

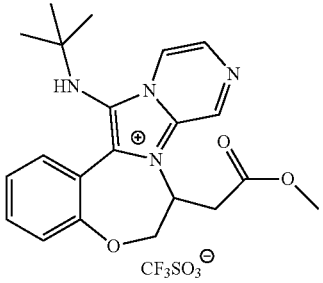

14-(tert-butylamino)-7-(2-methoxy-2-oxoethyl)-6,7-dihydrobenzo[f]pyrazino[2',1':2,3]imidazo[1,5-d][1,4]oxazepin-8-ium trifluoromethanesulfonate Pale yellow color solid, 137 mg, 52%. $^1$H NMR (500 MHz, MeOD) δ 9.74 (s, 1H), 8.87 (dd, J=4.5, 1.1 Hz, 1H), 8.56 (d, J=4.5 Hz, 1H), 8.40 (dd, J=8.0, 1.1 Hz, 1H), 7.57 (dd, J=11.4, 4.1 Hz, 1H), 7.27 (dd, J=13.5, 8.0 Hz, 2H), 6.04-5.95 (m, 1H), 5.00 (s, 0.7H), 4.82 (dd, J=13.1, 3.7 Hz, 1H), 4.74-4.66 (m, 1H), 3.60 (s, 3H), 3.14-3.04 (m, 1H), 2.84-2.73 (m, 1H), 1.12 (s, 9H). $^{13}$C NMR (125 MHz, MeOD) δ 170.5, 155.0, 137.9, 133.9, 133.1, 1317, 131.2, 130.0, 127.6, 122.4, 120.8, 117.5, 113.5, 72.5, 56.8, 55.4, 51.3, 33.3, 28.9. HRMS (ESI-TOF): m/z calcd for $C_{22}H_{25}F_3N_4O_6S$ 530.1446, found 381.1962 [M-CF$_3$SO$_3$]$^+$.

Compound 1b had the following chemical formula and characterization data:

Compound 1b

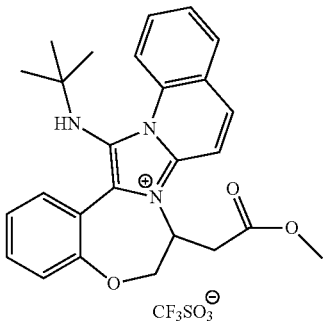

16-(tert-butylamino)-7-(2-methoxy-2-oxoethyl)-6,7-dihydrobenzo[6′,7′][1,4]oxazepino[4′,5′:3,4]imidazo[1,2-a]quinolin-8-ium trifluoromethanesulfonate Off white color solid, 133 mg, 46%. $^1$H NMR (500 MHz, MeOD) δ 10.14 (d, J=8.8 Hz, 1H), 8.44 (d, J=9.5 Hz, 1H), 8.21 (d, J=9.3 Hz, 2H), 8.07 (d, J=7.6 Hz, 1H), 7.99 (t, J=7.7 Hz, 1H), 7.84 (t, J=7.4 Hz, 1H), 7.61 (t, J=7.2 Hz, 1H), 7.42-7.27 (m, 2H), 5.96-5.84 (m, 1H), 5.16 (s, 1H), 4.71 (dd, J=12.7, 2.2 Hz, 1H), 3.55 (s, 3H), 2.98 (dd, J=17.7, 3.8 Hz, 1H), 2.71 (dd, J=17.7, 10.3 Hz, 1H), 1.01 (s, 9H). $^{13}$C NMR (125 MHz, MeOD) δ 170.3, 155.0, 136.9, 135.4, 133.6, 132.7, 131.6, 131.4, 130.4, 129.8, 129.4, 127.6, 125.1, 123.7, 121.1, 119.2, 116.9, 108.8, 73.9, 56.8, 54.2, 51.2, 34.9, 28.4. HRMS (ESI-TOF): m/z calcd for $C_{27}H_{28}F_3N_3O_6S$ 579.1650, found 430.2156 [M-CF$_3$SO$_3$]$^+$.

Compound 1c had the following chemical formula and characterization data:

Compound 1c

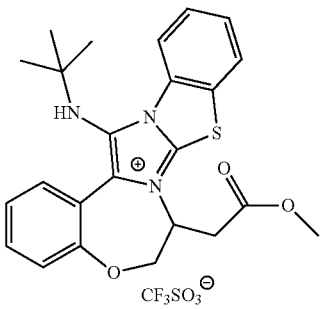

15-(tert-butylamino)-7-(2-methoxy-2-oxoethyl)-6,7-dihydrobenzo[f]benzo[4′,5′]thiazolo[2′,3′:2,3]imidazo[1,5-d][1,4]oxazepin-8-ium trifluoromethanesulfonate Off white color solid, 152 mg, 52%. $^1$H NMR (500 MHz, MeOD) δ 8.75 (d, J=8.3 Hz, 1H), 8.19 (d, J=8.1 Hz, 1H), 8.07 (dd, J=7.8, 1.4 Hz, 1H), 7.82-7.77 (m, 1H), 7.75-7.69 (m, 1H), 7.59-7.52 (m, 1H), 7.35-7.24 (m, 2H), 5.30 (dt, J=8.0, 3.8 Hz, 1H), 5.07 (s, 0.5H), 4.79 (dd, J=12.7, 3.2 Hz, 1H), 4.67 (dd, J=12.7, 4.8 Hz, 1H), 3.66 (s, 3H), 3.08 (dd, J=18.0, 3.7 Hz, 1H), 2.90 (dd, J=18.0, 10.2 Hz, 1H), 1.15-1.05 (m, 9H). $^{13}$C NMR (125 MHz, MeOD) δ 170.3, 154.3, 132.4, 132.3, 131.0, 130.9, 130.7, 129.5, 127.5, 127.4, 124.7, 123.4, 121.7, 121.1, 119.1, 117.0, 73.1, 58.3, 56.4, 51.5, 33.50, 28.78. HRMS (ESI-TOF): m/z calcd for $C_{25}H_{26}F_3N_3O_6S_2$ 585.1215, found 436.1732 [M-CF$_3$SO$_3$]$^+$.

Compound 1d had the following chemical formula and characterization data:

Compound 1d

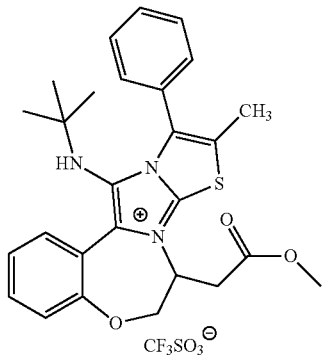

13-(tert-butylamino)-7-(2-methoxy-2-oxoethyl)-10-methyl-11-phenyl-6,7-dihydrobenzo[f]thiazolo[2′,3′:2,3]imidazo[1,5-d][1,4]oxazepin-8-ium trifluoromethanesulfonate Off white color solid, 171 mg, 55%. $^1$H NMR (500 MHz, MeOD) δ 8.06 (dd, J=7.8, 1.3 Hz, 1H), 7.69-7.62 (m, 5H), 7.52-7.44 (m, 1H), 7.25-7.14 (m, 2H), 5.29-5.22 (m, 1H), 4.73-4.63 (m, 2H), 3.70 (s, 3H), 3.58 (s, 0.8H), 3.10 (dd, J=18.1, 3.5 Hz, 1H), 2.89 (dd, J=18.1, 10.4 Hz, 1H), 2.49 (s, 3H), 0.53 (s, 9H). $^{13}$C NMR (126 MHz, MeOD) δ 172.0, 155.7, 144.9, 133.3, 132.8, 132.5, 132.4, 131.5, 131.1, 131.0, 130.0, 128.8, 128.5, 124.2, 122.0, 117.3, 74.1, 59.9, 56.7, 52.9, 34.76, 29.6, 13.00. HRMS (ESI-TOF): m/z calcd for $C_{28}H_{30}F_3N_3O_6S_2$ 625.1528, found 476.2058 [M-CF$_3$SO$_3$]$^+$.

Compound 1e had the following chemical formula and characterization data:

Compound 1e

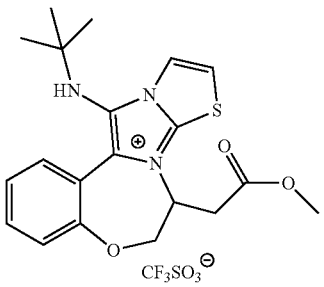

13-(tert-butylamino)-7-(2-methoxy-2-oxoethyl)-6,7-dihydrobenzo[f]thiazolo[2′,3′:2,3]imidazo[1,5-d][1,4]oxazepin-8-ium trifluoromethanesulfonate Off white color solid, 120 mg, 45%. $^1$H NMR (500 MHz, MeOD) δ 8.25 (d, J=8.0 Hz, 1H), 8.15 (d, J=4.3 Hz, 1H), 7.70 (t, J=5.8 Hz, 1H), 7.51-7.46 (m, 1H), 7.28-7.17 (m, 2H), 5.29-5.23 (m, 1H), 4.79 (s, 0.5H), 4.68-4.64 (m, 2H), 3.67 (s, 3H), 3.09 (dd, J=18.0, 3.6 Hz, 1H), 2.89 (dd, J=18.0, 10.3 Hz, 1H), 1.10 (s, 9H). $^{13}$C NMR (125 MHz, MeOD) δ 170.6, 154.2, 145.1, 131.8, 130.6, 129.4, 128.1, 122.7, 120.8, 120.1, 117.7, 115.9, 72.4, 58.4, 56.0, 51.5, 33.3, 28.7. HRMS (ESI-TOF): m/z calcd for $C_{21}H_{24}F_3N_3O_6S_2$ 535.1058, found 386.1058 [M-CF$_3$SO$_3$]$^+$.

Compound 1f had the following chemical formula and characterization data:

Compound 1f

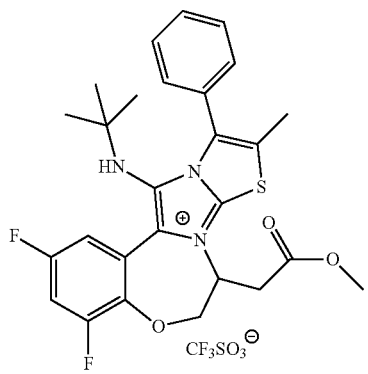

13-(tert-butylamino)-2,4-difluoro-7-(2-methoxy-2-oxoethyl)-10-methyl-11-phenyl-6,7-dihydrobenzo[f]thiazolo[2′,3′:2,3]imidazo[1,5-d][1,4]oxazepin-8-ium trifluoromethanesulfonate Off white color solid, 148 mg, 45%. $^1$H NMR (500 MHz, MeOD) δ 7.75 (d, J=9.3 Hz, 1H), 7.31-7.23 (m, 1H), 5.34-5.27 (m, 1H), 4.80-4.69 (m, 2H), 3.71 (s, 3H), 3.63 (s, 1H), 3.14 (dd, J=18.0, 3.7 Hz, 1H), 2.97 (dd, J=18.0, 10.1 Hz, 1H), 2.49 (s, 3H), 0.57 (s, 9H). $^{13}$C NMR (126 MHz, MeOD) δ 170.4, 157.2 (d, $^1J_{C-F}$=244.0 Hz), 154.3 (d, $^1J_{C-F}$=252.0 Hz), 144.1, 139.2, 131.1, 130.9, 130.3, 130.2, 128.7, 127.9, 127.6, 126.9, 112.0, 106.7, 106.5, 73.4, 57.9, 55.7, 51.2, 33.5, 28.3. HRMS (ESI-TOF): m/z calcd for $C_{28}H_{28}F_5N_3O_6S_2$ 661.1339, found 512.1819 [M-CF$_3$SO$_3$]$^+$.

Compound 1g had the following chemical formula and characterization data:

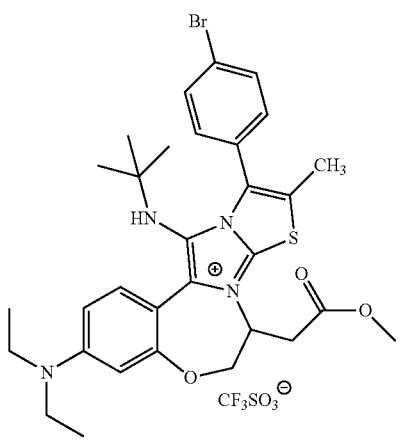

Compound 1g 11-(4-bromophenyl)-13-(tert-butylamino)-3-(diethylamino)-7-(2-methoxy-2-oxoethyl)-10-methyl-6,7-dihydrobenzo[f]thiazolo[2′,3′:2,3]imidazo[1,5-d][1,4]oxazepin-8-ium trifluoromethanesulfonate Off white color solid, 185 mg, 48%. $^1$H NMR (500 MHz, MeOD) δ 7.79 (d, J=8.4 Hz, 2H), 7.74 (d, J=9.0 Hz, 1H), 7.56 (d, J=8.4 Hz, 2H), 6.55 (dd, J=9.0, 2.3 Hz, 1H), 6.38 (d, J=2.3 Hz, 1H), 5.21-5.14 (m, 1H), 4.65-4.55 (m, 2H), 3.70 (s, 3H), 3.44 (q, J=7.0 Hz, 2H), 3.09 (dd, J=18.0, 3.3 Hz, 1H), 2.95 (dd, J=18.0, 10.3 Hz, 1H), 2.48 (s, 3H), 1.21 (t, J=7.0 Hz, 6H), 0.59 (s, 9H). $^{13}$C NMR (125 MHz, MeOD) δ 170.8, 155.8, 150.7, 142.2, 133.0, 132.1, 132.0, 131.4, 130.1, 127.6, 127.3, 126.3, 123.9, 106.6, 101.1, 100.9, 72.1, 58.6, 54.8, 51.4, 43.9, 33.0, 28.4, 11.6, 11.4. LCMS (ESI): m/z 626 [M-CF$_3$SO$_3$]$^+$.

Compound 1h had the following chemical formula and characterization data:

Compound 1h

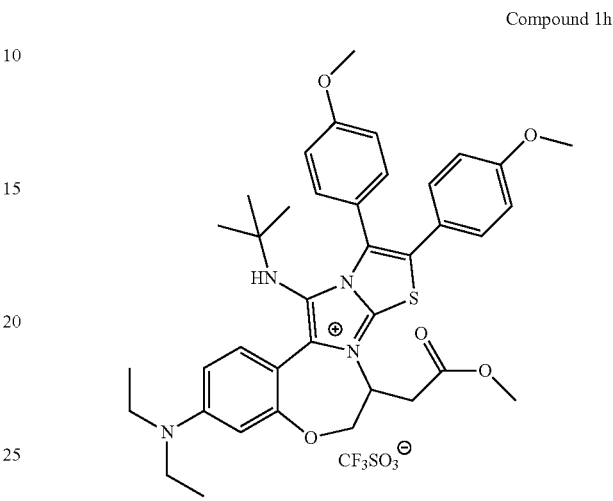

13-(tert-butylamino)-3-(diethylamino)-7-(2-methoxy-2-oxoethyl)-10,11-bis(4-methoxyphenyl)-6,7-dihydrobenzo[f]thiazolo[2′,3′:2,3]imidazo[1,5-d][1,4]oxazepin-8-ium trifluoromethanesulfonate Pale brown color solid, 184 mg, 44%. $^1$H NMR (500 MHz, MeOD) δ 7.84 (d, J=9.0 Hz, 1H), 7.49-7.40 (m, 2H), 7.27-7.22 (m, 2H), 7.07 (d, J=8.1 Hz, 2H), 6.96-6.92 (m, 2H), 6.58-6.52 (m, 1H), 6.38 (d, J=2.5 Hz, 1H), 5.25-5.18 (m, 1H), 4.66-4.59 (m, 2H), 3.87 (s, 3H), 3.82 (s, 3H), 3.69 (s, 3H), 3.45 (q, J=7.0 Hz, 2H), 3.11 (dd, J=18.1, 3.4 Hz, 1H), 2.98 (dd, J=18.1, 10.3 Hz, 1H), 1.21 (t, J=7.0 Hz, 7H), 0.61 (s, 9H). $^{13}$C NMR (125 MHz, MeOD) δ 172.3, 162.7, 162.3, 157.1, 152.0, 143.7, 134.3, 133.6, 132.4, 132.2, 131.4, 130.8, 129.4, 122.4, 120.6, 115.6, 115.4, 108.0, 102.4, 102.1, 73.3, 60.1, 56.5, 56.0, 55.9, 52.9, 45.3, 34.4, 29.9, 12.8. LCMS (ESI): m/z 626 [M-CF$_3$SO$_3$]$^+$.

Compound 1i had the following chemical formula and characterization data:

Compound 1i

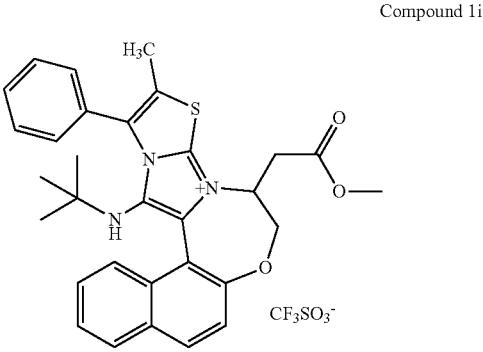

15-(tert-butylamino)-9-(2-methoxy-2-oxoethyl)-12-methyl-13-phenyl-8,9-dihydronaphtho[1,2-f]thiazolo[2′,3′:2,3]imidazo[1,5-d][1,4]oxazepin-10-ium trifluoromethanesulfonate Off white color solid, 162 mg, 48%. Mixture of diastereoisomers (64:36). $^1$H NMR (500 MHz, CDCl$_3$) δ 8.06 (d, J=8.4 Hz, 0.36H), 8.01 (d, J=8.8 Hz, 0.36H), 7.97 (d, J=8.8 Hz, 0.66H), 7.93-7.86 (m, 1.8H), 7.71-7.50 (m, 6H), 7.36-7.29 (m, 1H), 5.46-5.36 (m, 0.66H), 5.14-5.05 (dd, J=12.4, 6.2 Hz, 0.66H), 5.05-4.97 (m, 0.36H), 4.66-4.56 (m, 0.66H), 4.46 (d, J=12.4 Hz, 0.66H), 3.84 (dd, J=16.7, 5.8 Hz, 0.36H), 3.71 (s, 3H), 3.57 (s, 2H), 3.17 (dd, J=16.7, 8.5 Hz, 0.36H), 2.70-2.48 (m, 2.2H), 2.42 (two s, 3H), 0.18 (two s, 9H). LCMS (ESI): m/z 526 [M-CF$_3$SO$_3$]$^+$.

Compound 1j had the following chemical formula and characterization data:

Compound 1j

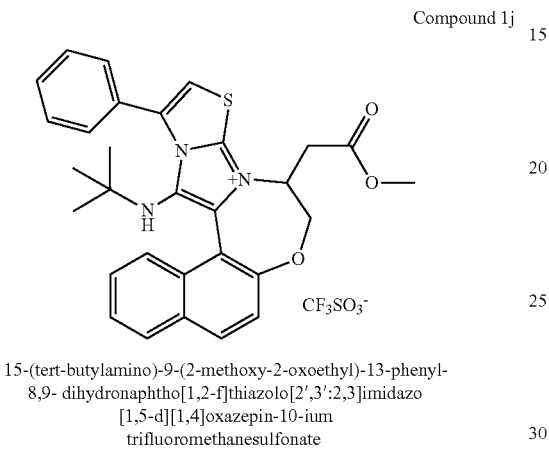

15-(tert-butylamino)-9-(2-methoxy-2-oxoethyl)-13-phenyl-8,9- dihydronaphtho[1,2-f]thiazolo[2′,3′:2,3]imidazo[1,5-d][1,4]oxazepin-10-ium trifluoromethanesulfonate Off white color solid, 99 mg, 30%. Mixture of diastereoisomers (64:36). $^1$H NMR (500 MHz, CDCl$_3$) δ 8.15-7.99 (m, 2H), 7.94 (dd, J=8.1, 2.6 Hz, 1H), 7.84-7.72 (m, 3H), 7.64-7.54 (m, 4H), 7.43-7.30 (m, 2H), 5.52-5.39 (m, 0.64H), 5.19-5.05 (m, 1H), 4.68-4.60 (m, 0.72H), 4.54-4.47 (m, 0.64H), 3.90-3.80 (m, 0.6H), 3.73 (s, 1.2H), 3.60 (s, 1.8H), 3.24-3.17 (m, 0.4H), 2.85-2.58 (m, 2H), 2.66 (t, J=18.0 Hz, 1H), 0.21 (two s, 9H). LCMS (ESI): m/z 512 [M-CF$_3$SO$_3$]$^+$.

Compound 1k had the following chemical formula and characterization data:

Compound 1k

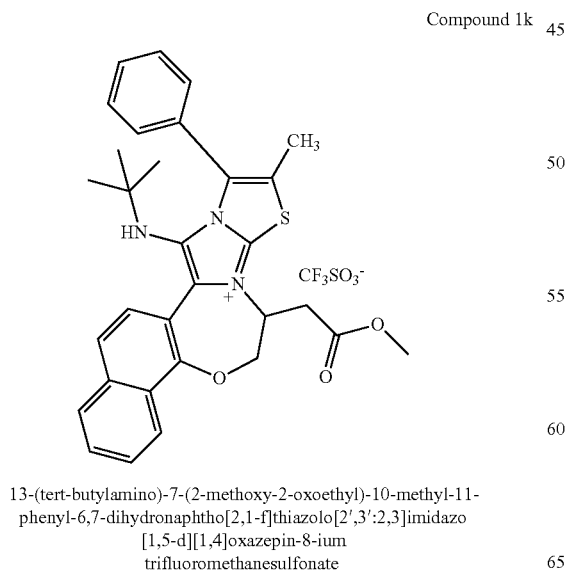

13-(tert-butylamino)-7-(2-methoxy-2-oxoethyl)-10-methyl-11-phenyl-6,7-dihydronaphtho[2,1-f]thiazolo[2′,3′:2,3]imidazo[1,5-d][1,4]oxazepin-8-ium trifluoromethanesulfonate Pale yellow color solid, 172 mg, 51%. $^1$H NMR (500 MHz, CDCl$_3$) δ 8.30 (dd, J=8.2, 0.8 Hz, 1H), 8.09 (d, J=8.9 Hz, 1H), 7.79-7.76 (m, 1H), 7.68-7.51 (m, 7H), 7.47 (d, J=8.9 Hz, 1H), 5.47-5.40 (m, 1H), 5.03-4.94 (m, 2H), 3.69 (s, 3H), 3.06-2.91 (m, 2H), 2.43 (s, 3H), 0.56 (s, 9H). $^{13}$C NMR (125 MHz, CDCl$_3$) δ 171.2, 150.0, 144.7, 135.0, 130.8, 130.0, 129.80, 128.3, 128.2, 128.0, 127.5, 127.3, 127.3, 126.7, 126.3, 123.2, 121.9, 108.4, 72.9, 59.8, 57.3, 52.6, 33.5, 29.6, 13.2. LCMS (ESI): m/z 526 [M-CF$_3$SO$_3$]$^+$.

Compound 1l had the following chemical formula and characterization data:

Compound 1l

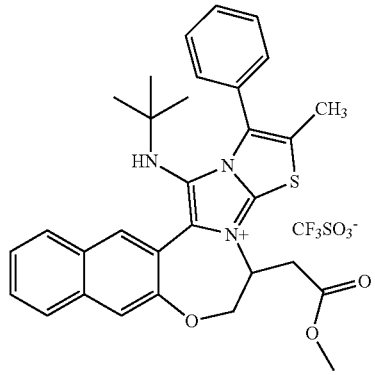

14-(tert-butylamino)-5-(2-methoxy-2-oxoethyl)-2-methyl-1-phenyl-5,6-dihydronaphtho[2,3-f]thiazolo[2′,3′:2,3]imidazo[1,5-d][1,4]oxazepin-4-ium trifluoromethanesulfonate Off white color solid, 185 mg, 55%. $^1$H NMR (500 MHz, CDCl$_3$) δ 8.60 (s, 1H), 7.97 (d, J=8.1 Hz, 1H), 7.79 (d, J=8.1 Hz, 1H), 7.70-7.45 (m, 7H), 7.28 (s, 1H), 5.30-5.21 (m, 1H), 4.95-4.86 (m, 1H), 4.58-4.50 (m, 1H), 3.67 (s, 3H), 3.14 (s, 0.9H), 3.02 (dd, J=17.7, 8.3 Hz, 1H), 2.81 (dd, J=17.7, 3.9 Hz, 1H), 2.45 (s, 3H), 0.47 (s, 9H). $^{13}$C NMR (126 MHz, CDCl$_3$) δ 170.4, 151.4, 142.9, 135.1, 132.2, 131.5, 131.4, 130.7, 130.4, 130.2, 129.5, 129.2, 128.8, 128.3, 127.1, 126.9, 126.8, 126.2, 119.2, 117.9, 74.8, 56.8, 56.1, 52.7, 35.9, 29.6, 13.3. LCMS (ESI): m/z 526 [M-CF$_3$SO$_3$]$^+$.

Compound 1m had the following chemical formula and characterization data:

Compound 1m

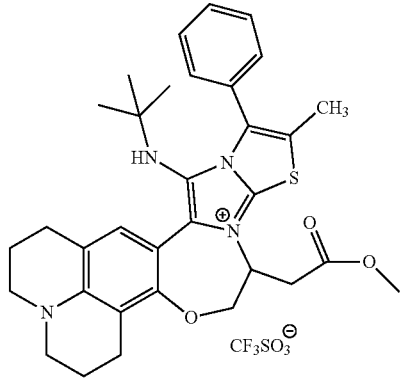

12-(tert-butylamino)-6-(2-methoxy-2-oxoethyl)-9-methyl-10-phenyl-2,3,5,6,15,16-hexahydro-1H,14H-pyrido[3,2,1-ij]thiazolo[2″,3″;2′,3′]imidazo[1′,5′:4,5][1,4]oxazepino[7,6-f]quinolin-7-ium trifluoromethanesulfonate Pale yellow color solid, 194 mg, 54%. $^1$H NMR (500 MHz, MeOD) δ 7.65-7.58 (m, 5H), 7.30 (s, 1H), 5.17-5.10 (m, 1H), 4.63 (dd, J=12.3, 4.3 Hz, 1H), 4.49 (dd, J=12.3, 4.7 Hz, 1H), 3.68 (s, 3H), 3.28-3.21 (m, 4H), 3.03-2.89 (m, 2H), 2.80-2.72 (m, 4H), 2.46 (s, 1H), 2.02-1.92 (m, 4H), 0.53 (s, 9H). $^{13}$C NMR (126 MHz, MeOD) δ 170.5, 150.3, 145.6, 141.5, 132.0, 131.21, 131.19, 129.9, 128.3, 127.7, 127.4, 127.2, 126.3, 117.1, 111.9, 104.1, 72.6, 57.0, 54.8, 51.4, 49.42, 48.9, 34.0, 28.4, 26.9, 21.5, 20.8, 20.7, 11.5. HRMS (ESI-TOF): m/z calcd for $C_{34}H_{39}F_3N_4O_6S_2$ 720.2263, found 571.2742 [M-CF$_3$SO$_3$]$^+$.

Compound 1n had the following chemical formula and characterization data:

Compound 1n

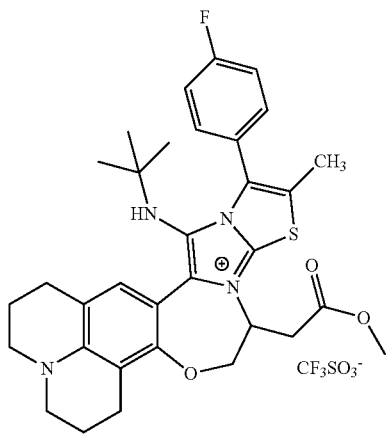

12-(tert-butylamino)-10-(4-fluorophenyl)-6-(2-methoxy-2-oxoethyl)-9-methyl-2,3,5,6,15,16-hexahydro-1H,14H-pyrido[3,2,1-ij]thiazolo[2″,3″:2′,3′]imidazo[1′,5′:4,5][1,4]oxazepino[7,6-f]quinolin-7-ium trifluoromethanesulfonate Pale yellow color solid, 202 mg, 55%. $^1$H NMR (500 MHz, Acetone) δ 7.83-7.76 (m, 1H), 7.43-7.37 (m, 2H), 5.30-5.24 (m, 1H), 4.79 (dd, J=12.5, 3.5 Hz, 1H), 4.69 (dd, J=12.5, 5.0 Hz, 1H), 3.69 (s, 0.8H), 3.67 (s, 3H), 3.27-3.21 (m, 4H), 3.15 (dd, J=18.0, 3.9 Hz, 1H), 3.04 (dd, J=18.0, 10.0 Hz, 1H), 2.78-2.69 (m, 4H), 2.53 (s, 3H), 2.00-1.89 (m, 4H), 0.60 (s, 9H). $^{13}$C NMR (126 MHz, Acetone) δ 170.4, 163.5, 150.4, 145.5, 141.9, 133.9, 132.5, 130.3, 128.1, 127.7, 127.6, 126.8, 123.7, 116.6, 115.5, 111.3, 103.1, 72.6, 57.8, 55.0, 54.9, 51.7, 49.5, 48.9, 33.9, 26.9, 21.6, 21.0, 20.9, 12.2. HRMS (ESI-TOF): m/z calcd for $C_{34}H_{38}F_4N_4O_6S_2$ 738.2168, found 589.2635 [M-CF$_3$SO$_3$]$^+$.

Compound 1o had the following chemical formula and characterization data:

Compound 1o

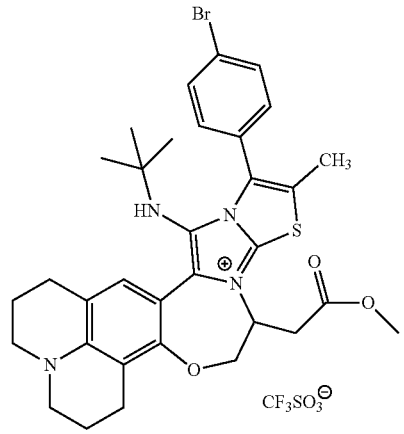

10-(4-bromophenyl)-12-(tert-butylamino)-6-(2-methoxy-2-oxoethyl)-9-methyl-2,3,5,6,15,16-hexahydro-1H,14H-pyrido[3,2,1-ij]thiazolo[2″,3″:2′,3′]imidazo[1′,5′:4,5][1,4]oxazepino[7,6-f]quinolin-7-ium trifluoromethanesulfonate Pale yellow color solid, 231 mg, 58%. $^1$H NMR (500 MHz, MeOD) δ 7.77 (d, J=8.5 Hz, 2H), 7.55 (d, J=8.4 Hz, 2H), 7.26 (s, 1H), 5.17-5.09 (m, 1H), 4.63 (dd, J=12.3, 4.5 Hz, 1H), 4.47 (dd, J=12.3, 4.7 Hz, 1H), 3.75 (s, 0.5H), 3.67 (s, 3H), 3.33 (dt, J=3.2, 1.6 Hz, 1H), 3.29-3.21 (m, 2H), 3.03-2.88 (m, 2H), 2.82-2.72 (m, 4H), 2.47 (s, 3H), 2.07-1.90 (m, 4H), 0.56 (s, 9H). $^{13}$C NMR (125 MHz, MeOD) δ 170.5, 150.32, 145.7, 141.5, 133.2, 132.6, 131.3, 130.1, 127.6, 127.4, 126.9, 126.2, 123.9, 117.2, 112.0, 104.1, 72.7, 56.9, 54.7, 51.4, 49.4, 48.9, 34.1, 28.5, 26.9, 21.5, 20.8, 20.7, 11.6. HRMS (ESI-TOF): m/z calcd for $C_{34}H_{37}BrF_3N_4O_6S_2$ 797.1290, found 649.1700 [M-CF$_3$SO$_3$]$^+$.

Compound 1p had the following chemical formula and characterization data:

Compound 1p

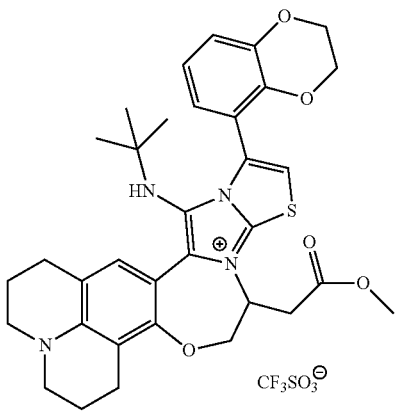

12-(tert-butylamino)-10-(2,3-dihydrobenzo[b][1,4]dioxin-5-yl)-6-(2-methoxy-2-oxoethyl)-2,3,5,6,15,16-hexahydro-1H,14H-pyrido[3,2,1-ij]thiazolo[2″,3″:2′,3′]imidazo[1′,5′:4,5][1,4]oxazepino[7,6-f]quinolin-7-ium trifluoromethanesulfonate Light green color solid, 183 mg, 48%. $^1$H NMR (500 MHz, MeOD) δ 7.40 (s, 1H), 7.34 (s, 1H), 7.25 (d, J=1.9 Hz, 1H), 7.17 (dd, J=8.3, 2.0 Hz, 1H), 7.02 (d, J=8.3 Hz, 1H), 5.20-5.11 (m, 1H), 4.63 (dd, J=12.3, 4.4 Hz, 1H), 4.48 (dd, J=12.3, 4.6 Hz, 1H), 4.38-4.30 (m, 4H), 3.87 (s, 0.3H), 3.66 (s, 3H), 3.30-3.21 (m, 4H), 3.04-2.94 (m, 2H), 2.82-2.73 (m, 4H), 2.04-1.91 (m, 4H), 0.63 (s, 9H). $^{13}$C NMR (125 MHz, MeOD) δ 170.5, 150.4, 145.6, 144.3, 143.5, 136.2, 132.7, 127.9, 127.4, 123.3, 120.7, 119.4, 117.19, 117.16, 116.8, 112.9, 111.9, 104.1, 72.6, 64.6, 64.3, 57.0, 55.0, 51.4, 49.4, 48.9, 34.1, 28.4, 26.9, 21.5, 20.8, 20.7. HRMS (ESI-TOF): m/z calcd for $C_{35}H_{39}F_3N_4O_8S_2$ 764.2161, found 615.2616 $[M-CF_3SO_3]^+$.

Compound 1q had the following chemical formula and characterization data:

Compound 1q

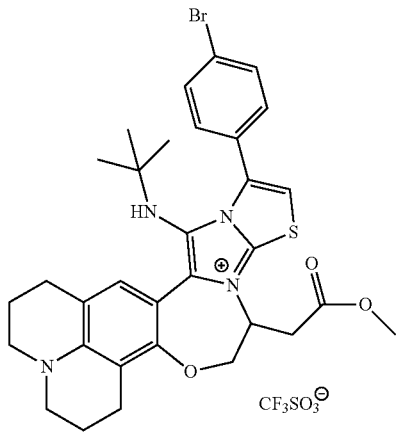

10-(4-bromophenyl)-12-(tert-butylamino)-6-(2-methoxy-2-oxoethyl)-2,3,5,6,15,16-hexahydro-1H,14H-pyrido[3,2,1-ij]thiazolo[2″,3″:2′,3′]imidazo[1′,5′:4,5][1,4]oxazepino[7,6-f]quinolin-7-ium trifluoromethanesulfonate Off white color solid, 199 mg, 51%. $^1$H NMR (500 MHz, MeOD) δ 7.74 (d, J=8.3 Hz, 1H), 7.66 (d, J=8.3 Hz, 1H), 7.56 (s, 1H), 7.29 (s, 1H), 5.22-5.14 (m, 1H), 4.65 (dd, J=12.3, 4.4 Hz, 1H), 4.49 (dd, J=12.3, 4.6 Hz, 1H), 3.66 (s, 3H), 3.31-3.22 (m, 4H), 3.04-2.91 (m, 2H), 2.84-2.72 (m, 4H), 2.02-1.94 (m, 4H), 0.58 (s, 9H). $^{13}$C NMR (126 MHz, MeOD) δ 170.5, 150.4, 145.8, 144.4, 135.4, 133.5, 132.1, 131.1, 127.7, 127.3, 127.2, 124.0, 117.3, 114.5, 112.1, 104.1, 72.7, 57.0, 54.9, 51.4, 49.4, 48.9, 34.1, 28.4, 26.9, 21.4, 20.8, 20.7. LCMS (ESI): m/z 635 $[M-CF_3SO_3]^+$.

Compound 1r had the following chemical formula and characterization data:

Compound 1r

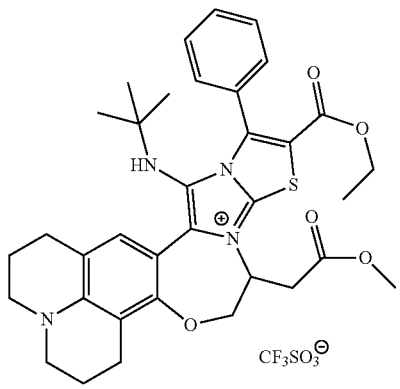

12-(tert-butylamino)-9-(ethoxycarbonyl)-6-(2-methoxy-2-oxoethyl)-10-phenyl-2,3,5,6,15,16-hexahydro-1H,14H-pyrido[3,2,1-ij]thiazolo[2″,3″:2′,3′]imidazo[1′,5′:4,5][1,4]oxazepino[7,6-f]quinolin-7-ium trifluoromethanesulfonate Pale yellow color solid, 210 mg, 54%. $^1$H NMR (500 MHz, MeOD) δ 7.78-7.54 (m, 5H), 7.31 (s, 1H), 5.28-5.18 (m, 1H), 4.66 (dd, J=12.5, 4.9 Hz, 1H), 4.52 (dd, J=12.5, 4.2 Hz, 1H), 4.33-4.21 (m, 2H), 3.69 (s, 3H), 3.44 (s, 0.6H), 3.29-3.21 (m, 1H), 3.02 (dd, J=18.1, 3.8 Hz, 1H), 2.91 (dd, J=18.1, 10.1 Hz, 1H), 2.80-2.70 (m, 4H), 2.03-1.92 (m, 4H), 1.20 (t, J=7.1 Hz, 3H), 0.55 (s, 9H). $^{13}$C NMR (126 MHz, MeOD) δ 170.7, 159.4, 150.4, 145.8, 143.4, 139.8, 133.0, 132.4, 130.6, 128.3, 127.8, 127.7, 126.4, 121.1, 117.0, 111.6, 103.0, 72.3, 62.5, 57.6, 54.9, 51.5, 49.4, 48.9, 34.0, 28.5, 28.3, 26.8, 21.4, 20.8, 12.7. LCMS (ESI): m/z 629 $[M-CF_3SO_3]^+$.

Compound 1s had the following chemical formula and characterization data:

Compound 1s

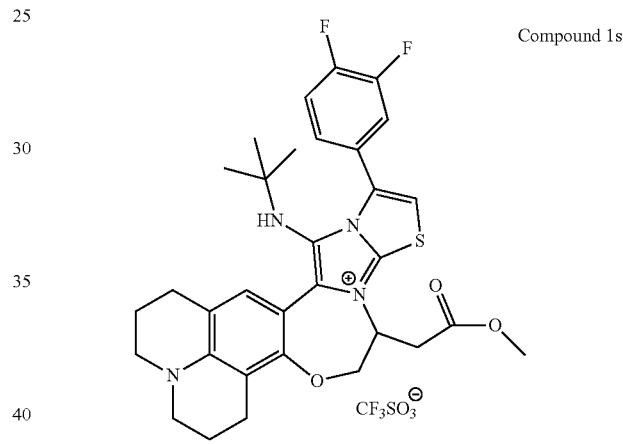

12-(tert-butylamino)-10-(3,4-difluorophenyl)-6-(2-methoxy-2-oxoethyl)-2,3,5,6,15,16-hexahydro-1H,14H-pyrido[3,2,1-ij]thiazolo[2″,3″:2′,3′]imidazo[1′,5′:4,5][1,4]oxazepino[7,6-f]quinolin-7-ium trifluoromethanesulfonate Off white color solid, 210 mg, 54%. $^1$H NMR (500 MHz, MeOD) δ 7.81-7.74 (m, 1H), 7.63-7.43 (m, 3H), 7.28 (s, 1H), 5.22-5.14 (m, 1H), 4.66 (dd, J=12.3, 4.5 Hz, 1H), 4.48 (dd, J=12.3, 4.6 Hz, 1H), 4.19 (s, 0.8H), 3.66 (s, 3H), 3.31-3.22 (m, 4H), 3.08-2.88 (m, 2H), 2.85-2.71 (m, 4H), 2.06-1.92 (m, 4H), 0.61 (s, 9H). $^{13}$C NMR (126 MHz, MeOD) δ 171.8, 152.9, 151.8 (d, $^1J_{C-F}$=243 Hz), 150.9 (d, $^1J_{C-F}$=249.0 Hz), 147.2, 145.7, 135.7, 135.0, 129.2, 128.8, 128.7, 126.6, 121.5, 118.7, 118.3, 116.5, 113.6, 105.5, 74.1, 58.4, 56.3, 52.8, 50.8, 50.3, 35.5, 29.8, 28.3, 22.8, 22.2, 22.1. LCMS (ESI): m/z 593 $[M-CF_3SO_3]^+$.

Compound 1t had the following chemical formula and characterization data:

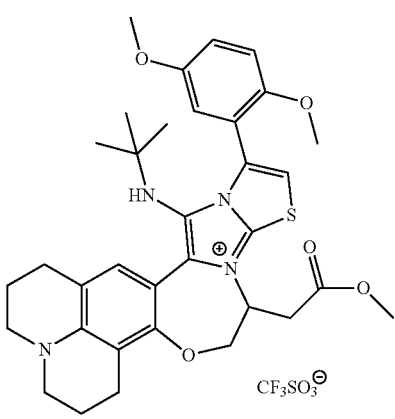

Compound 1t 12-(tert-butylamino)-10-(2,5-dimethoxyphenyl)-6-(2-methoxy-2-oxoethyl)-2,3,5,6,15,16-hexahydro-1H,14H-pyrido[3,2,1-ij]thiazolo[2″,3″:2′,3′]imidazo[1′,5′:4,5][1,4]oxazepino[7,6-f]quinolin-7-ium trifluoromethanesulfonate Off white color solid, 183 mg, 48%. $^1$H NMR (500 MHz, MeOD) δ 7.47 (s, 1H), 7.35 (s, 1H), 7.18 (ddd, J=16.5, 8.2, 2.7 Hz, 3H), 5.20-5.12 (m, 1H), 4.62 (dd, J=12.3, 4.0 Hz, 1H), 4.55-4.46 (m, 1H), 3.86 (s, 3H), 3.84 (s, 3H), 3.68 (s, 3H), 3.40 (s, 0.3H), 3.29-3.19 (m, 4H), 3.09-2.90 (m, 2H), 2.83-2.72 (m, 4H), 2.05-1.93 (m, 4H), 0.60 (s, 9H). $^{13}$C NMR (126 MHz, MeOD) δ 170.5, 154.0, 151.8, 150.4, 145.6, 143.7, 132.6, 131.7, 127.7, 127.5, 117.9, 117.8, 117.0, 116.8, 114.8, 112.2, 111.7, 103.8, 72.4, 55.5, 55.1, 54.9, 51.4, 49.4, 48.9, 28.5, 26.9, 21.5, 20.85, 20.77. LCMS (ESI): m/z 617 [M-CF$_3$SO$_3$]$^+$.

Compound 1u had the following chemical formula and characterization data:

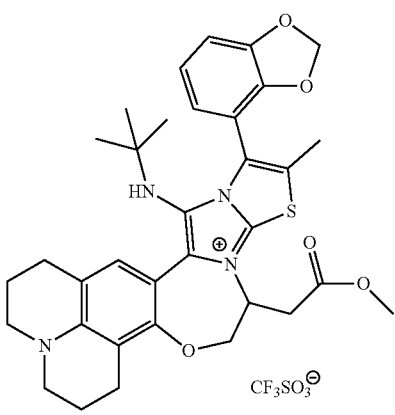

Compound 1u 10-(benzo[d][1,3]dioxol-4-yl)-12-(tert-butylamino)-6-(2-methoxy-2-oxoethyl)-9-methyl-2,3,5,6,15,16-hexahydro-1H,14H-pyrido[3,2,1-ij]thiazolo[2″,3″:2′,3′]imidazo[1′,5′:4,5][1,4]oxazepino[7,6-f]quinolin-7-ium trifluoromethanesulfonate Pale yellow color solid, 194 mg, 51%. $^1$H NMR (500 MHz, MeOD) δ 7.30 (s, 1H), 7.13 (d, J=1.5 Hz, 1H), 7.11-7.03 (m, 2H), 6.14-6.07 (m, 2H), 5.15-5.08 (m, 1H), 4.62 (dd, J=12.3, 4.0 Hz, 1H), 4.48 (dd, J=12.3, 4.7 Hz, 1H), 3.67 (s, 3H), 3.28-3.20 (m, 4H), 3.03-2.86 (m, 2H), 2.80-2.73 (m, 4H), 2.46 (s, 3H), 2.03-1.92 (m, 4H), 0.62 (s, 9H).

$^{13}$C NMR (125 MHz, MeOD) δ 170.5, 150.3, 149.4, 148.0, 145.6, 141.4, 131.8, 131.0, 127.7, 127.5, 126.0, 125.5, 120.3, 117.1, 111.9, 111.4, 107.9, 104.1, 101.9, 72.6, 57.0, 54.8, 51.4, 49.4, 48.9, 28.6, 26.9, 21.5, 20.8, 20.7, 11.6.

Compound 1v had the following chemical formula and characterization data:

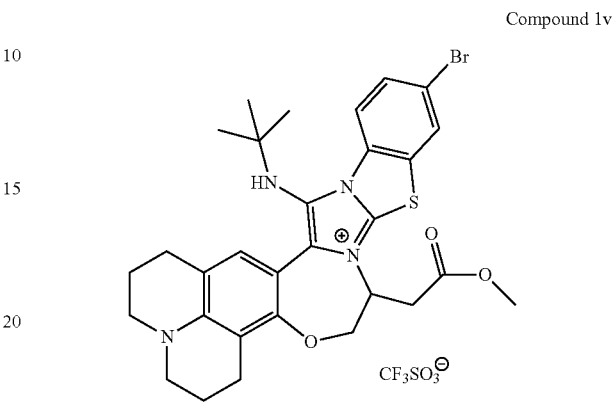

Compound 1v 14-bromo-18-(tert-butylamino)-10-(2-methoxy-2-oxoethyl)-2,3,6,7,9,10-hexahydro-1H,5H-benzo[4″,5″]thiazolo[2″,3″:2′,3′]imidazo[1′,5′:4,5][1,4]oxazepino[7,6-f]pyrido[3,2,1-ij]quinolin-11-ium trifluoromethanesulfonate Pale yellow color solid, 185 mg, 49%. $^1$H NMR (500 MHz, MeOD) δ 8.65 (d, J=8.8 Hz, 1H), 8.40 (d, J=1.8 Hz, 1H), 7.92 (dd, J=8.8, 1.9 Hz, 1H), 7.30 (s, 1H), 5.24-5.14 (m, 1H), 4.71 (dd, J=12.1, 4.7 Hz, 1H), 4.47 (dd, J=12.1, 4.5 Hz, 1H), 3.63 (s, 3H), 3.31-3.21 (m, 4H), 3.03-2.87 (m, 2H), 2.87-2.73 (m, 4H), 2.07-1.93 (m, 4H), 1.11 (s, 9H). $^{13}$C NMR (125 MHz, MeOD) δ 170.3, 150.3, 145.9, 142.8, 133.3, 131.6, 131.0, 130.6, 128.7, 127.3, 127.0, 119.9, 118.0, 117.5, 112.4, 104.3, 72.8, 57.1, 56.0, 51.4, 49.4, 48.9, 34.2, 28.9, 26.9, 21.4, 20.7, 20.6. LCMS (ESI): m/z 609 [M-CF$_3$SO$_3$]$^+$.

Compound 1w had the following chemical formula and characterization data:

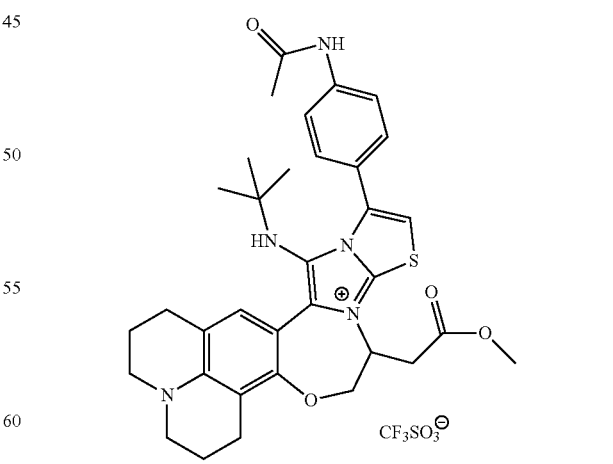

Compound 1w 10-(4-acetamidophenyl)-12-(tert-butylamino)-6-(2-methoxy-2-oxoethyl)-2,3,5,6,15,16-hexahydro-1H,14H-pyrido[3,2,1-ij]thiazolo[2″,3″:2′,3′]imidazo[1′,5′:4,5][1,4]oxazepino[7,6-f]quinolin-7-ium trifluoromethanesulfonate Pale yellow color solid, 171 mg, 45%. $^1$H NMR (500 MHz, MeOD) δ 7.79 (d, J=8.6 Hz, 1H), 7.67 (d, J=8.6 Hz, 1H), 7.45 (s, 1H), 7.32 (s, 1H), 5.22-5.13 (m, 1H), 4.64 (dd, J=12.3, 4.4 Hz, 1H), 4.49 (dd, J=12.3, 4.7 Hz, 1H), 3.94 (s, 0.3H), 3.66 (s, 3H), 3.29-3.21 (m, 4H), 3.05-2.90 (m, 2H), 2.84-2.72 (m, 4H), 2.19 (s, 3H), 2.05-1.94 (m, 4H), 0.58 (s, 9H). $^{13}$C NMR (126 MHz, MeOD) δ 170.5, 170.4, 150.4, 145.7, 144.3, 140.5, 136.3, 133.0, 130.8, 127.8, 127.4, 123.2, 118.8, 117.2, 113.3, 112.0, 104.1, 72.6, 57.0, 55.0, 51.4, 49.4, 48.9, 34.1, 28.4, 26.9, 22.6, 21.5, 20.8, 20.7. LCMS (ESI): m/z 609 [M-CF$_3$SO$_3$]$^+$.

Compound 1x had the following chemical formula and characterization data:

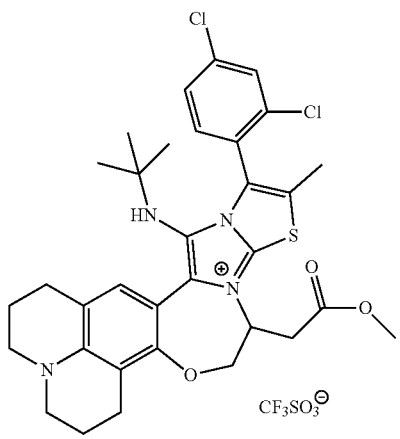

Compound 1x 12-(tert-butylamino)-10-(2,4-dichlorophenyl)-6-(2-methoxy-2-oxoethyl)-9-methyl-2,3,5,6,15,16-hexahydro-1H,14H-pyrido[3,2,1-ij]thiazolo[2″,3″:2′,3′]imidazo[1′,5′:4,5][1,4]oxazepino[7,6-f]quinolin-7-ium trifluoromethanesulfonate Pale yellow color solid, 228 mg, 58%. $^1$H NMR (500 MHz, MeOD) δ 7.77 (d, J=1.9 Hz, 1H), 7.73-7.66 (m, 1H), 7.59 (dd, J=8.3, 1.9 Hz, 1H), 7.21 (s, 1H), 5.13-5.07 (m, 1H), 4.60 (dd, J=11.9, 4.6 Hz, 2H), 4.46 (dd, J=11.9, 6.0 Hz, 1H), 3.69 (s, 3H), 3.62 (s, 0.4H), 3.29-3.21 (m, 4H), 3.07-3.00 (m, 2H), 2.82-2.73 (m, 4H), 2.41 (s, 3H), 2.03-0.93 (m, 4H), 0.59 (s, 9H). $^{13}$C NMR (125 MHz, MeOD) δ 171.6, 151.5, 147.2, 142.0, 138.4, 137.6, 136.2, 134.5, 130.7, 130.3, 128.8, 128.8, 128.5, 128.2, 126.6, 118.8, 113.9, 106.1, 74.5, 57.7, 55.8, 52.9, 50.8, 50.3, 34.9, 30.1, 28.3, 22.8, 22.1, 22.0, 13.0. LCMS (ESI): m/z 639 [M-CF$_3$SO$_3$]$^+$.

Compound 1y had the following chemical formula and characterization data:

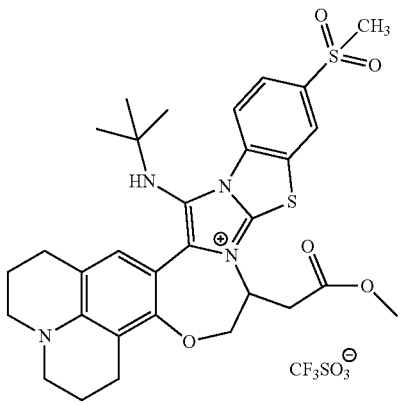

Compound 1y 18-(tert-butylamino)-10-(2-methoxy-2-oxoethyl)-14-(methylsulfonyl)-2,3,6,7,9,10-hexahydro-1H,5H-benzo[4″,5″]thiazolo[2″,3″:2′,3′]imidazo[1′,5′:4,5][1,4]oxazepino[7,6-f]pyrido[3,2,1-ij]quinolin-11-ium trifluoromethanesulfonate Pale yellow color solid, 94 mg, 25%. $^1$H NMR (500 MHz, MeOD) δ 8.96 (d, J=8.7 Hz, 1H), 8.83 (d, J=1.5 Hz, 1H), 8.31 (dd, J=8.7, 1.7 Hz, 1H), 8.21 (d, J=1.7 Hz, 1H), 7.81 (dd, J=8.5, 1.9 Hz, 1H), 7.52 (d, J=8.5 Hz, 1H), 7.32 (s, 1H), 5.27-5.20 (m, 1H), 4.73 (dd, J=12.2, 4.7 Hz, 1H), 4.50 (dd, J=12.2, 4.4 Hz, 1H), 3.64 (s, 3H), 3.31-3.25 (m, 4H), 3.13 (s, 3H), 3.04-2.91 (m, 2H), 2.86-2.76 (m, 4H), 2.06-1.95 (m, 4H), 1.12 (s, 9H). $^{13}$C NMR (125 MHz, MeOD) δ 171.7, 151.7, 147.4, 145.8, 141.1, 137.0, 135.2, 131.9, 130.3, 128.4, 127.9, 126.4, 126.2, 118.9, 113.8, 105.5, 74.1, 58.7, 57.5, 52.8, 50.8, 50.3, 44.4, 35.6, 30.3, 28.3, 22.8, 22.1, 22.1. LCMS (ESI): m/z 609 [M-CF$_3$SO$_3$]$^+$.

Compound 1z had the following chemical formula and characterization data:

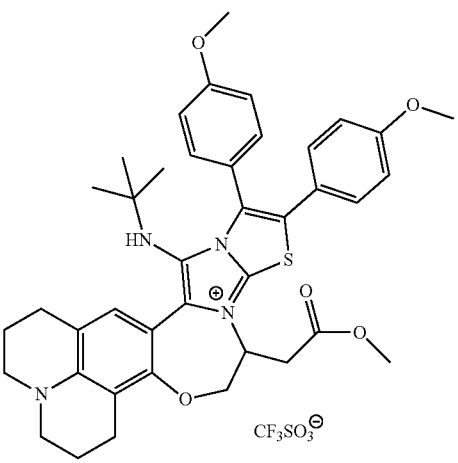

Compound 1z 12-(tert-butylamino)-6-(2-methoxy-2-oxoethyl)-9,10-bis(4-methoxyphenyl)-2,3,5,6,15,16-hexahydro-1H,14H-pyrido[3,2,1-ij]thiazolo[2″,3″:2′,3′]imidazo[1′,5′:4,5][1,4]oxazepino[7,6-f]quinolin-7-ium trifluoromethanesulfonate Pale yellow color solid, 227 mg, 54%. $^1$H NMR (500 MHz, MeOD) δ 7.50-7.41 (m, 2H), 7.34 (s, 1H), 7.24 (d, J=8.2 Hz, 1H), 7.06 (d, J=7.6 Hz, 1H), 6.93 (d, J=8.2 Hz, 1H), 5.23-5.13 (m, 1H), 4.71-4.63 (m, 1H), 4.52 (dd, J=12.1, 3.8 Hz, 1H), 3.87 (s, 3H), 3.81 9s, 3H), 3.66 (s, 3H), 3.20-3.21 (m, 4H), 3.07-2.97 (m, 2H), 2.84-2.72 (m, 4H), 2.05-1.93 (m, 4H), 0.58 (s, 9H). $^{13}$C NMR (125 MHz, MeOD) δ 172.0, 162.7, 162.3, 151.8, 147.0, 143.0, 134.5, 133.2, 132.3, 131.5, 130.4, 129.4, 128.9, 122.4, 120.6, 118.5, 115.6, 115.2, 113.2, 105.4, 74.0, 58.5, 56.4, 56.0, 55.9, 52.8, 50.8, 50.3, 35.5, 30.0, 28.3, 22.9, 22.2, 22.1. LCMS (ESI): m/z 693 [M-CF$_3$SO$_3$]$^+$.

Compound 2a had the following chemical formula and characterization data:

Compound 2a

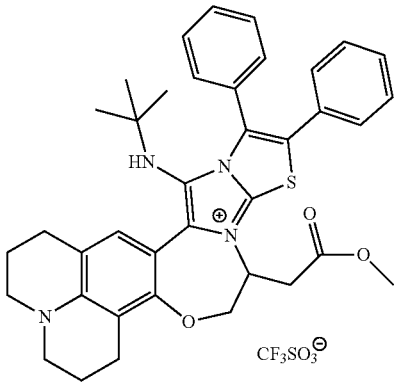

12-(tert-butylamino)-6-(2-methoxy-2-oxoethyl)-9,10-diphenyl-2,3,5,6,15,16-hexahydro-1H,14H-pyrido[3,2,1-ij]thiazolo[2″,3″:2′,3′]imidazo[1′,5′:4,5][1,4]oxazepino[7,6-f]quinolin-7-ium trifluoromethanesulfonate Pale yellow color solid, 218 mg, 56%. $^1$H NMR (500 MHz, MeOD) δ 7.63-7.47 (m, 5H), 7.46-7.28 (m, 6H), 5.26-5.17 (m, 1H), 4.68 (dd, J=12.3, 4.1 Hz, 1H), 4.53 (dd, J=12.3, 4.4 Hz, 1H), 3.67 (s, 1H), 3.60 (s, 0.3H), 3.30-3.20 (m, 4H), 3.07-2.91 (m, 2H), 2.83-2.71 (m, 4H), 2.05-1.93 (m, 4H), 0.55 (s, 9H). $^{13}$C NMR (125 MHz, MeOD) δ 170.6, 150.4, 145.7, 142.0, 132.2, 131.8, 130.8, 130.0, 129.9 (2C), 129.6, 129.0, 128.8, 128.4, 128.0, 127.6, 127.3, 117.1, 111.8, 103.8, 72.5, 57.3, 54.8, 51.4, 49.4, 48.9, 34.0, 28.5, 26.9, 21.5, 20.8, 20.7. LCMS (ESI): m/z 633 [M-CF$_3$SO$_3$]$^+$.

Compound 2b had the following chemical formula and characterization data:

Compound 2b

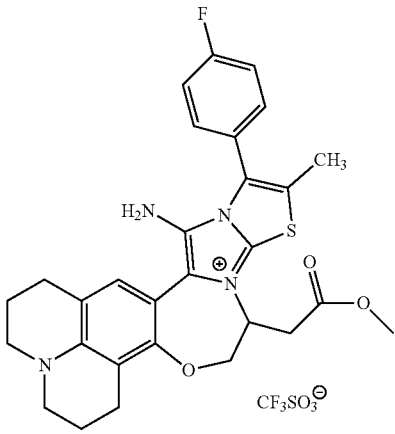

12-amino-10-(4-fluorophenyl)-6-(2-methoxy-2-oxoethyl)-9-methyl-2,3,5,6,15,16-hexahydro-1H,14H-pyrido[3,2,1-ij]thiazolo[2″,3″:2′,3′]imidazo[1′,5′:4,5][1,4]oxazepino[7,6-f]quinolin-7-ium trifluoromethanesulfonate Pale brown color solid, 184 mg, 44%. $^1$H NMR (500 MHz, MeOD) δ 7.67 (dd, J=8.8, 5.2 Hz, 1H), 7.36 (t, J=8.7 Hz, 1H), 7.04 (s, 1H), 5.13-5.05 (m, 1H), 4.60 (dd, J=12.4, 3.8 Hz, 1H), 4.53-4.45 (m, 1H), 4.48 (dd, J=12.4, 4.7 Hz, 1H), 3.68 (s, 3H), 3.27-3.16 (m, 4H), 3.03-2.98 (m, 1H), 2.95-2.88 (m, 1H), 2.78-2.70 (m, 4H), 2.39 (s, 3H), 2.03-1.91 (m, 4H). $^{13}$C NMR (125 MHz, MeOD) δ 172.0, 166.4, 164.4, 151.4, 146.2, 140.6, 134.7, 130.4, 130.2, 127.7, 127.0, 123.9, 123.9, 121.9, 118.5, 117.1, 116.9, 113.5, 104.6, 73.4, 58.6, 52.8, 50.9, 50.3, 35.2, 28.3, 22.9, 22.3, 22.3, 12.8. LCMS (ESI): m/z 533 [M-CF$_3$SO$_3$]$^+$.

Example 2

In a second experimental example, novel compounds of general formula B were prepared and characterized. In this experimental example, an aldehyde (general formula IV, 0.5 mmol), 2-aminoazine (general formula II, 0.5 mmol), scandium triflate (20 mol %), and sodium sulfate (1.0 mmol) were mixed in ACN (2 mL) at room temperature. After 45 mins, isocyanide (general formula III, 0.55 mmol) was introduced and stirring was continued at room temperature for 12-15 hours. After completion of step-1 (Groebuk reaction), ytterbium triflate was added (30 mol %) and continued the reaction at 70° C. for 3 to 12 hours. After completion of step-2 (Michael reaction), ACN was removed and the obtained crude material was purified on flash column chromatography using a gradient of EtOAC/hexane or MeOH/DCM as mobile phase eluents to obtain pure products of general formula B.

Compound 2c had the following chemical formula and characterization data:

Compound 2c

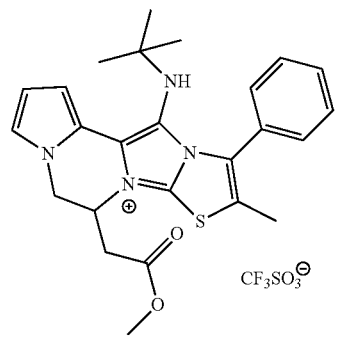

12-(tert-butylamino)-6-(2-methoxy-2-oxoethyl)-9-methyl-10-phenyl-5,6-dihydropyrrolo[1,2-a]thiazolo[2′,3′:2,3]imidazo[5,1-c]pyrazin-7-ium trifluoromethanesulfonate Pale yellow color solid, 167 mg, 55%. $^1$H NMR (500 MHz, MeOD) δ 7.64-7.57 (m, 5H), 7.02-6.98 (m, 1H), 6.86 (d, J=2.9 Hz, 1H), 6.36-6.27 (m, 1H), 5.41-5.35 (m, 1H), 4.60-4.48 (m, 2H), 3.92 (s, 0.7H), 3.71 (s, 3H), 2.92 (dd, J=17.4, 4.5 Hz, 1H), 2.70 (dd, J=17.4, 8.5 Hz, 1H), 2.48 (s, 3H), 0.70 (s, 9H). $^{13}$C NMR (125 MHz, MeOD) δ 170.6, 141.8, 131.4, 131.3, 129.8, 128.1, 127.0, 126.7, 125.3, 124.3, 122.9, 117.0, 109.4, 109.2, 56.0, 52.8, 51.5, 48.1, 35.1, 28.8, 11.8. HRMS (ESI-TOF): m/z calcd for C$_{26}$H$_{29}$F$_3$N$_4$O$_5$S$_2$ 598.1531, found 449.2060 [M-CF$_3$SO$_3$]$^+$.

Compound 2d had the following chemical formula and characterization data:

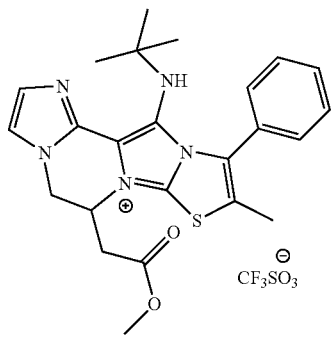

Compound 2d 12-(tert-butylamino)-6-(2-methoxy-2-oxoethyl)-9-methyl-10-phenyl-5,6-dihydroimidazo[1,2-a]thiazolo[2',3':2,3]imidazo[5,1-c]pyrazin-7-ium trifluoromethanesulfonate Off white color solid, 152 mg, 51%. $^1$H NMR (500 MHz, MeOD) δ 7.66-7.57 (m, 5H), 7.43 (d, J=3.1 Hz, 1H), 7.30-7.25 (m, 1H), 5.57-5.48 (m, 1H), 4.78-4.65 (m, 2H), 3.72 (s, 3H), 2.97 (dd, J=17.5, 3.6 Hz, 1H), 2.77 (dd, J=17.5, 8.3 Hz, 1H), 2.50 (s, 3H), 0.70 (s, 9H). $^{13}$C NMR (125 MHz, MeOD) δ 170.4, 143.6, 134.0, 131.6, 131.5, 129.8, 129.2, 129.1, 127.8, 127.7, 126.5, 121.0, 119.9, 56.3, 52.5, 51.6, 35.20, 28.10, 12.02. HRMS (ESI-TOF): m/z calcd for $C_{25}H_{28}F_3N_5O_5S_2$ 599.1483, found 450.1976 [M-CF$_3$SO$_3$]$^+$.

Compound 2e had the following chemical formula and characterization data:

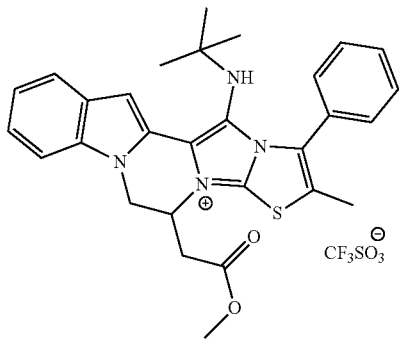

Compound 2e 13-(tert-butylamino)-5-(2-methoxy-2-oxoethyl)-2-methyl-1-phenyl-5,6-dihydrothiazolo[2'',3'':2',3']imidazo[5',1':3,4]pyrazino[1,2-a]indol-4-ium trifluoromethanesulfonate Off white color solid, 145 mg, 45%. $^1$H NMR (500 MHz, MeOD) δ 7.70-7.60 (m, 6H), 7.53 (d, J=8.2 Hz, 1H), 7.32 (t, J=7.2 Hz, 1H), 7.27 (s, 1H), 7.18 (t, J=7.2 Hz, 1H), 5.58-5.52 (m, 1H), 4.95 (dd, J=13.5, 1.4 Hz, 1H), 4.53 (dd, J=13.5, 3.8 Hz, 1H), 3.65 (s, 3H), 2.97 (dd, J=17.3, 4.4 Hz, 1H), 2.77 (dd, J=17.3, 8.4 Hz, 1H), 2.51 (s, 3H), 0.75 (s, 9H). $^{13}$C NMR (125 MHz, MeOD) δ 170.6, 142.7, 136.6, 131.4, 131.3, 129.9 (2C), 128.2, 128.0, 127.3, 126.9, 123.5, 123.4, 122.6, 121.1, 120.7, 109.0, 102.1, 56.6, 53.1, 51.4, 35.4, 28.8, 11.9. HRMS (ESI-TOF): m/z calcd for $C_{30}H_{31}F_3N_4O_5S_2$ 648.1687, found 499.2147 [M-CF$_3$SO$_3$]$^+$.

Example 3

In a third experimental example, the compounds prepared in Examples 1 and 2 were tested for potential antibacterial activities against the Gram-negative bacteria *Escherichia coli* (ATCC 25922) and *Pseudomonas aeruginosa* (ATCC 27853) and the Gram-positive bacteria *Staphylococcus aureus* (ATCC 25923), *Enterococcus faecalis* (ATCC 29212), and *Bacillus subtilis* (environmental isolate). The results of the assay used to test the disclosed compounds for antibacterial effects on *Staphylococcus aureus* (ATCC 25923) are shown in FIG. 1. Specifically, the compounds shown in FIG. 1 were each tested in duplicate and pink and blue colors were used to differentiate viable from dead bacterial suspensions, respectively. Two compounds (1o and 2a) in wells A6 and B9 (red arrows) exhibited positive antibacterial activities. The background color of the test compound is responsible for the dark pink to red color in A7 wells (no antibacterial activity). Two standard antibiotics (ciprofloxacin and amikacin) were used in serial dilution as positive controls. Blank (media only), growth (untreated), and vehicle (DMSO) controls were also included in each experiment. Positive controls included two standard antibiotics (ciprofloxacin and amikacin) used in 2-fold serial dilutions (10 concentrations started from 8 and 32 μg/mL for ciprofloxacin and amikacin, respectively). The black circles represent MICs for ciprofloxacin and amikacin (0.5 and 4 μg/mL, respectively).

Cost-effective and fast methods for high throughput simultaneous screening of multiple compounds were used to screen the disclosed compounds. While broth microdilution is the standard method for testing minimum inhibitory concentrations, this method was modified to be used as a method for screening of multiple compounds simultaneously in a single 96-well microplate. As some of the tested compounds were colored, causing turbidity in the culture media, it was not possible to conclude the absence of bacterial growth by visual inspection of the media or by measuring the optical density. Therefore, a colorimetric assay "CellTiter-Blue® Cell Viability Assay (Promega, USA)" was used to test bacterial cell viability.

The Cell Viability Assay solution (Promega, USA) used contained resazurin dye, which was used to measure the metabolic capacity of cells as an indicator of cell viability. In microbiology, resazurin has been used as a growth indicator for *Mycobacterium tuberculosis* to facilitate MIC determination in this slowly growing microbe.

Resazurin has been used in some cell cytotoxicity studies. According to manufacturer instructions, the CellTiter-Blue® Cell Viability Assay (Promega, USA) is intended for cell cytotoxicity testing in both absorbance and fluorescence modes. However, it was used in the disclosed experiments to screen for potential antibacterial activities and MIC determination using colorimetric (visual) methods.

Resazurin is dark blue in color, but when it is reduced to resorufin, the solution becomes pink in color and highly fluorescent. Viable bacterial cells have the ability to reduce resazurin into resorufin, which is highly fluorescent; thus, viable cells can be differentiated from dead cells which do not reduce the indicator dye. A change of color from blue to pink indicates reduction of resazurin and therefore bacterial growth and viability. Absence of bacterial growth can be detected by absence of any color change (i.e., a solution that remains dark blue in color). In summary, a pink color (resazurin reduced to resorufin) indicates bacterial viability and blue color (non-reduced resazurin) indicates bacterial death.

This screening method can be applied for testing the antimicrobial activities of any colored chemical (including natural products) or chemicals causing turbidity in the culture media, mimicking microbial growth. The use of the growth indicator resazurin facilitates differentiation between live and dead microbes in response to a test chemical.

microbial growth following overnight incubation. The results of this testing are shown in Table 2 (below).

TABLE 2

MIC values (μg/mL) for selected compounds tested on S. aureus (ATCC 25923), 3 clinical isolates (MRSA) and 7 environmental isolates of the genus Staphylococcus

| Compound | S. aureus (ATCC 25923) | Clinical isolates | | | Environmental isolates | | | | | | |
|---|---|---|---|---|---|---|---|---|---|---|---|
| | | MRS A-1 | MRS A-2 | MRS A-3 | UD H-1 | UD H-2 | UD H-3 | UD H-4 | UD H-5 | UD H-6 | UD H-7 |
| 1h | 6.25 | 6.25 | 6.25 | 3.125 | 6.25 | 6.25 | 3.125 | 6.25 | 1.56 | 6.25 | 12.5 |
| 1n | 6.25 | 12.5 | 12.5 | 12.5 | 12.5 | 12.5 | 12.5 | 12.5 | 6.25 | 25 | 25 |
| 1o | 3.125 | 3.125 | 3.125 | 3.125 | 6.25 | 6.25 | 3.125 | 6.25 | 3.125 | 6.25 | 6.25 |
| 1p | 3.125 | 6.25 | 6.25 | 6.25 | 12.5 | 25 | 6.25 | 6.25 | 1.56 | 12.5 | 12.5 |
| 1q | 3.125 | 6.25 | 6.25 | 6.25 | 6.25 | 6.25 | 12.5 | 3.125 | 3.125 | 12.5 | 12.5 |
| 1r | 12.5 | 12.5 | 12.5 | 12.5 | 12.5 | 25 | 12.5 | 25 | 6.25 | 50 | 50 |
| 1s | 6.25 | 6.25 | 6.25 | 6.25 | 12.5 | 25 | 12.5 | 6.25 | 3.125 | 25 | 25 |
| 1t | 3.125 | 6.25 | 3.125 | 3.125 | 6.25 | 6.25 | 6.25 | 6.25 | 3.125 | 12.5 | 12.5 |
| 1u | 3.125 | 3.125 | 3.125 | 3.125 | 6.25 | 6.25 | 3.125 | 6.25 | 1.56 | 6.25 | 6.25 |
| 1v | 12.5 | 12.5 | 12.5 | 12.5 | 12.5 | 25 | 12.5 | 25 | 6.25 | 50 | 50 |
| 1w | 6.25 | 12.5 | 12.5 | 12.5 | 12.5 | 25 | 12.5 | 12.5 | 6.25 | 50 | 50 |
| 1x | 3.125 | 6.25 | 6.25 | 6.25 | 6.25 | 6.25 | 6.25 | 3.125 | 1.56 | 6.25 | 12.5 |
| 1z | 3.125 | 6.25 | 6.25 | 6.25 | 12.5 | 6.25 | 12.5 | 3.125 | 1.56 | 12.5 | 12.5 |
| 2a | 6.25 | 6.25 | 3.125 | 3.125 | 6.25 | 6.25 | 3.125 | 6.25 | 1.56 | 6.25 | 12.5 |
| 2b | 12.5 | 12.5 | 12.5 | 12.5 | 12.5 | 12.5 | 25 | 12.5 | 6.25 | 25 | 25 |
| Amikacin | 4 | 16 | 8 | 2 | 8 | 0.25 | 0.5 | <0.25 | <0.25 | 4 | 4 |
| Ciprofloxacin | 0.5 | 32 | 16 | 2 | 64 | 64 | 64 | 64 | <0.25 | 64 | 64 |

Table 1 (below) shows all the tested compounds that were active against all the three tested Gram-positive bacteria (*Staphylococcus aureus*, *Enterococcus faecalis*, and *Bacillus subtilis*).

TABLE 1

List of active compounds tested against the identified Gram-positive and Gram-negative bacteria

| | Bacterial species | | | | |
|---|---|---|---|---|---|
| Compound | Staphylococcus aureus | Enterococcus faecalis | Bacillus subtilis | Escherichia coli | Pseudomonas aeruginosa |
| 1h | Positive | Positive | Positive | Negative | Negative |
| 1n | Positive | Positive | Positive | Negative | Negative |
| 1o | Positive | Positive | Positive | Positive | Negative |
| 1p | Positive | Positive | Positive | Negative | Negative |
| 1q | Positive | Positive | Positive | Negative | Negative |
| 1r | Positive | Positive | Positive | Negative | Negative |
| 1s | Positive | Positive | Positive | Negative | Negative |
| 1t | Positive | Positive | Positive | Negative | Negative |
| 1u | Positive | Positive | Positive | Negative | Negative |
| 1v | Positive | Positive | Positive | Negative | Negative |
| 1w | Positive | Positive | Positive | Negative | Negative |
| 1x | Positive | Positive | Positive | Positive | Negative |
| 1z | Positive | Positive | Positive | Negative | Negative |
| 2a | Positive | Positive | Positive | Negative | Negative |
| 2b | Positive | Positive | Positive | Negative | Negative |

Each compound was tested at a single high concentration of 1 mg/mL. A positive result indicates antibacterial activity expressed as growth inhibition and a negative result indicates no antibacterial activity expressed as bacterial growth at the tested concentration. As shown in Table 1, two of compounds tested (1o and 1x) were also active against *E. coli* at a test concentration of 1 mg/mL.

The compounds exhibiting potential antibacterial activities in the screening phase were further tested for the minimum inhibitory concentrations (MIC), which is the lowest concentration of a chemical required to inhibit visible Bacteria of the genus *Staphylococcus* were selected for MIC investigation due to its clinical importance. Compounds showing activity against *S. aureus* (ATCC 25923) were tested against 10 multidrug-resistant strains of *Staphylococcus* species, including: clinical isolates methicillin-resistant *Staphylococcus aureus* (MRSA) strains MRSA-1, MRSA-2, and MRSA-3, and environmental isolates *S. saprophyticus* (strains UDH-1, UDH-2, UDH-3 and UDH-4), *S. haemolyticus* (strains UDH-6 and UDH-7), and *S. epidermidis* strain UDH-5.

All these strains were resistant to at least three antibiotics from different classes, as confirmed by a disk diffusion assay. The assay was performed according to the Clinical and Laboratory Standards Institute guidelines using the following antibiotic disks (Himedia, India): ceftriaxone (30 μg), cefoxitin (30 μg), cefepime (30 μg), cefpodoxime (10 μg), cefpodoxime/clavulanic acid (10 μg/5 μg), meropenem (10 μg), gentamicin (50 μg), ciprofloxacin (30 μg) and trimethoprim/sulphamethoxazole (1.25/23.75 μg). The results of this experiment are shown in Table 2.

MIC values of two quality control antibiotics (amikacin and ciprofloxacin) are also shown in Table 2. As shown in Table 2, the tested compounds exhibited bactericidal activity against all the tested strains (MBC/MIC ratio≤4).

The above results indicate that some of the disclosed compounds are 10-20 times more potent than ciprofloxacin, a commonly used antibiotic. For example, compounds 1o and 1u showed MICs of 3.125 μg/mL for the clinical strain MRSA-1 (*Staphylococcus aureus*), which is approximately 10 times lower than the MIC of ciprofloxacin (32 μg/mL). For the environmental strain UDH-1 (*S. saprophyticus*), compounds 1h, 1o, 1q, 1t, 1u, 1x, and 2a showed MICs of 6.25 μg/mL, which are approximately 10 times lower than MIC of ciprofloxacin (64 μg/mL). For the environmental strain UDH-3 (*S. saprophyticus*), compounds 1h, 1o, 1u, and 2a showed MICs of 3.125 μg/mL, which are approximately 20 times lower than MIC of ciprofloxacin (64 μg/mL). For the environmental strains UDH-6 and UDH-7 (*S. haemo-*

*lyticus*), compounds 1o and 1u showed MICs of 6.25 µg/mL, which are approximately 10 times lower than MIC of ciprofloxacin (64 µg/mL).

Example 4

Figure 2:
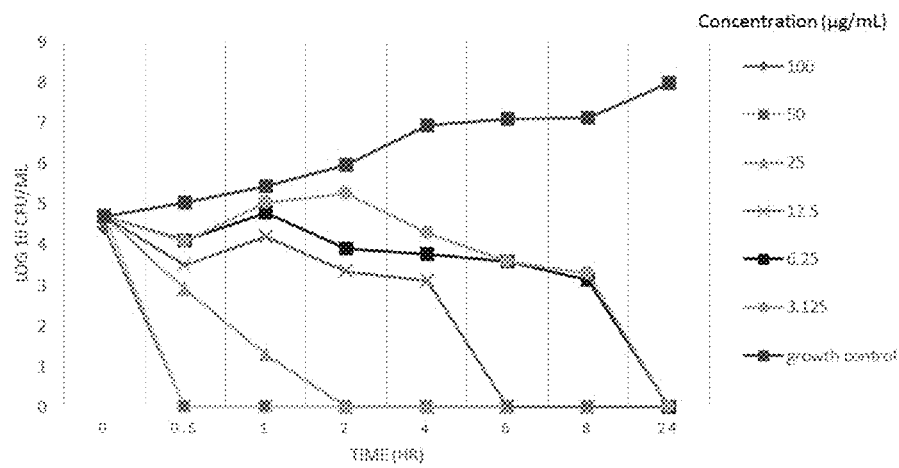
FIG. 2 shows a graph of experimental data from a time-kill experiment of MRSA-1 at different time points of exposure to compound 1o, in accordance with some embodiments of the subject disclosure.

A time-kill experiment for compound 1o revealed fast bactericidal activity with complete elimination of MRSA growth within 30 minutes of exposure to the compound at concentration≥50 µg/mL. The results of this experiment are shown in FIG. 2. As shown in FIG. 2, compound 1o was tested at concentrations between 3.125-100 µg/mL and killing was achieved at concentrations between 50-100 µg/mL after 30 minutes of exposure to the compound and at concentrations of 25 and 12.5 µg/mL after 2 and 6 hours of exposure to the compound, respectively. At lower concentrations (3.125-6.25 µg/mL), killing was achieved after 24 hours of exposure to the compound.

Figure 3:
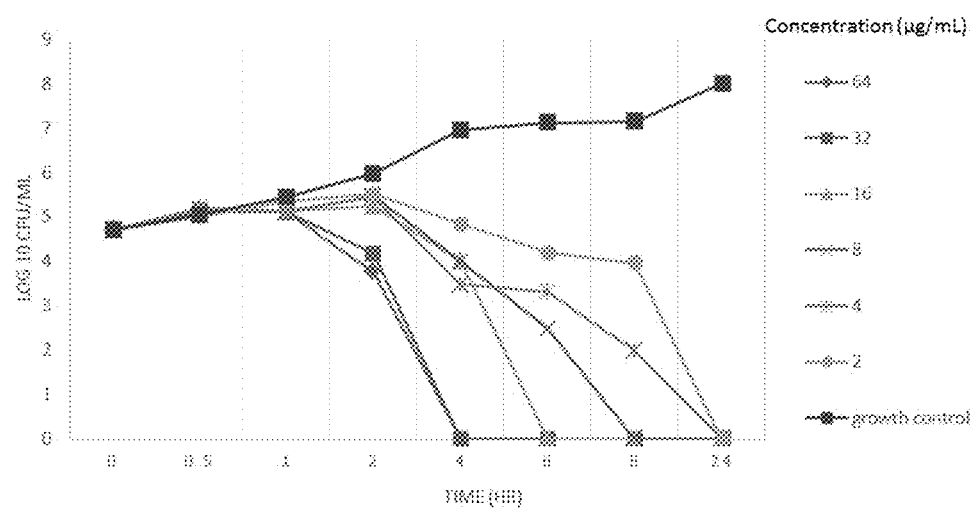
FIG. 3 shows a graph of experimental data from a time-kill experiment of MRSA-1 at different time points of exposure to meropenem.

In comparison, meropenem, a carbapenem which acts by inhibiting cell wall synthesis, was able to completely inhibit bacterial growth after 4 hours of exposure to the antibiotic at a concentration between 32-64 µg/mL (see FIG. 3). As shown in FIG. 3, meropenem was tested at concentrations between 2-64 µg/mL and killing was achieved at concentrations between 32-64 g/mL after 4 hours of exposure to the drug and at concentrations of 16 and 8 µg/mL after 6 and 8 hours of exposure to the drug, respectively. At lower concentrations (2-4 µg/mL), killing was achieved after 24 hours of exposure to the compound.

Figure 4:
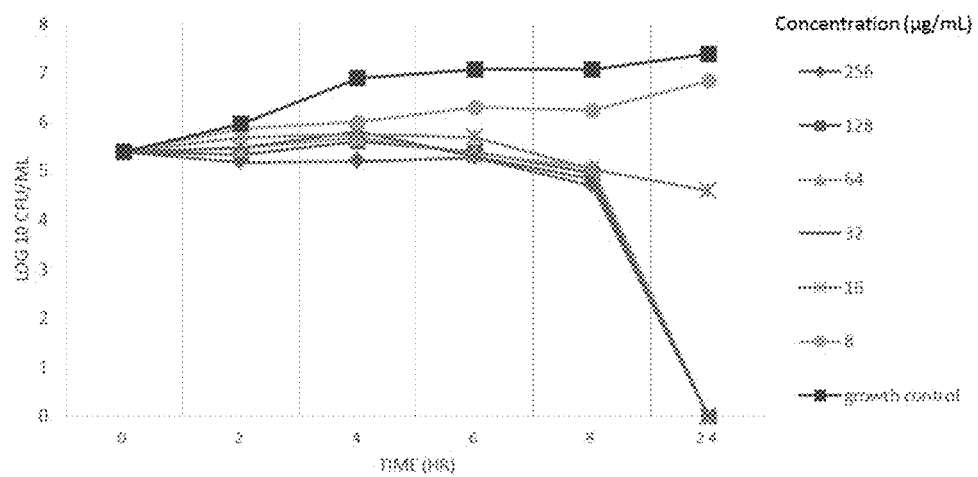
FIG. 4 shows a graph of experimental data from a time-kill experiment of MRSA-1 at different time points of exposure to ciprofloxacin.

Ciprofloxacin, a fluoroquinolone which acts intracellularly by inhibiting DNA synthesis, exhibited delayed killing effect with complete growth inhibition after 24 hours of exposure to the antibiotic at concentration between 32-256 µg/mL (see FIG. 4). As shown in FIG. 4, ciprofloxacin was tested at concentrations between 8-256 µg/mL and killing was achieved after 24 hours of exposure to the drug at concentrations between 32 and 256 µg/mL.

Example 5

Atomic force microscopy (AFM) provides three-dimensional images of the surfaces of living microbial cells in real time and in high resolution with minimal sample preparation. Compound 1o was tested against the bacterial strain MRSA-1 and the slides were examined under AFM. Specifically, FIGS. 5A1 and 5B1 show an untreated MRSA-1 strain at scan sizes of 10 µm$^2$ and m$^2$, respectively, and FIGS. 5A2 and 5B2 show a MRSA-1 strain treated with compound 1o at scan sizes of 10 µm$^2$ and 5 µm$^2$, respectively. Bacterial cell shape distortion and leakage of the intracellular contents are evident in FIGS. 5A2 and 5B2, suggesting cell wall damage caused by compound 1o. Rapid bacterial killing coupled with cell wall damage as evidenced in the AFM images indicate the action of compound 1o on the cell wall, as reported for the known antibiotics like polymyxin, which rapidly breaks the cell membrane of Gram-negative bacteria, causing fast cell death.

Example 5

Figure 6:
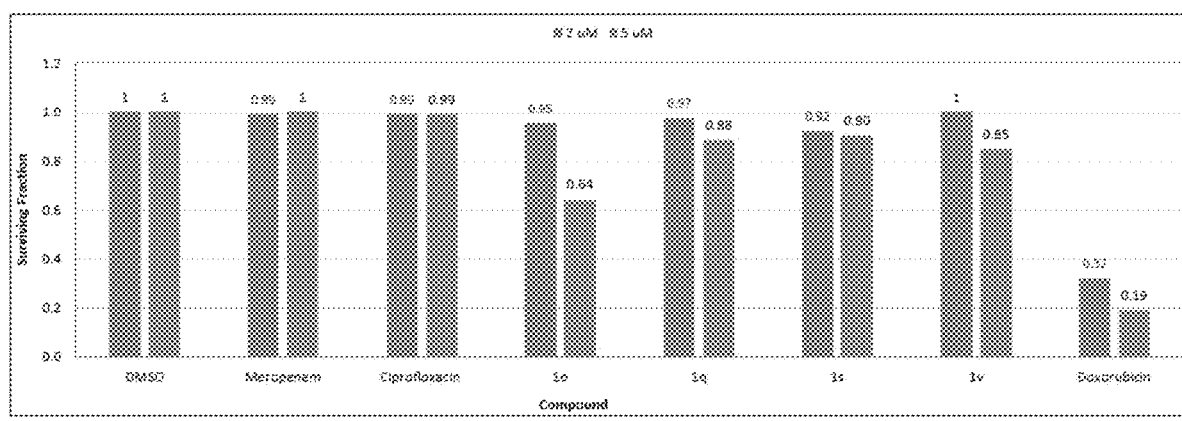
FIG. 6 shows a graph illustrating the effect of various disclosed compounds on the survival of normal human fibroblast cells (F180) at concentrations of 5 and 2 μM, in accordance with some embodiments of the subject disclosure.

The effect of the disclosed compounds on the survival of normal human fibroblast cells (F180) at different concentrations (2 and 5 µM) was tested by a sulforhodamine B (SRB) assay. The anticancer drug doxorubicin was used as a positive control and cells treated with DMSO served as a negative control. The antibiotics ciprofloxacin and meropenem were also included in the assay as controls. A surviving fraction of each compound was calculated in reference to the negative control (DMSO). The compounds were found safe because they had a lower effect on the survival of normal fibroblasts compared to the anticancer drug doxorubicin. FIG. 6 shows the experimental results of the surviving fraction of normal human fibroblast cells tested with some of the safe and presently disclosed compounds at concentration of 5 and 2 µM.

In the disclosed compositions, methods, and experimental examples, the compounds discussed were prepared as follows unless otherwise stated.

Chemistry:

Purchased chemical reagents and anhydrous solvents were used without further purification. Solvents for extraction and column chromatography were distilled prior to use. TLC analysis were performed with silica gel plates (0.25 mm, 60 F254) using iodine and a UV lamp for visualization. $^1$H and $^{13}$C NMR experiments were performed on a 400 MHz instrument, respectively. Chemical shifts are reported in parts per million (ppm) downstream from the internal tetramethylsilane standard. Spin multiplicities are described as s (singlet), bs (broad singlet), d (doublet), dd (double-doublet), t (triplet), q (quartet), or m (multiplet). Coupling constants are reported in Hertz (Hz). ESI mass spectrometry was performed on a Q-TOF high resolution mass spectrometer or Q-TOF Ultim LC-MS.

Screening the Compounds by the Cell Viability Assay:

Each test compound was dissolved in DMSO at a concentration of 100 mg/mL. A 96-well Microtiter™ microplate was filled with sterile Mueller-Hinton broth at a volume of 49 µL/well. Each compound was tested in duplicate by adding 1 µL of the compound solution into two adjacent wells. Then the volume was adjusted to 100 µL by adding 50 µL of the bacterial suspension containing 10$^6$ CFU/mL in Mueller-Hinton broth. Final compound concentration per well was 1 mg/mL and the final bacterial concentration was 5×10$^5$ CFU/mL. Two standard antibiotics (ciprofloxacin and amikacin) were used as positive controls. Blank (media only), growth (untreated) and vehicle (DMSO) controls were also included in each experiment.

A volume of 20 µL of the Cell Viability Assay solution was added to each well of the 96-well microplate containing bacteria pre-incubated with the test compounds (1 mg/mL) for 20 hours at 37° C. After the addition of the Cell Viability Assay solution, the 96-well microplate was incubated at 37° C. for 4 more hours. Pink and blue colors were used to differentiate viable from dead bacterial suspensions, respectively.

Minimum Inhibitory Concentrations (MIC) and Minimum Bactericidal Concentration (MBC):

A broth microdilution method was used to measure MIC according to the Clinical and Laboratory Standards Institute guidelines. Two-fold serial dilutions of the test compound (8 concentrations ranged between 100-0.78 µg/mL) were tested. Two reference antibiotics were used as quality controls (ciprofloxacin and amikacin). In each experiment, solvent (DMSO) was used as a negative control, un-treated control (composing of bacteria in Mueller-Hinton broth) was used as a growth control, blank (culture media alone) was used as sterility control. The 96-well microplate with the test compounds was incubated for 20 hours at 37° C. Turbidity in wells indicated bacterial growth. MIC was recorded as the lowest concentration of a compound that completely inhibited any visible bacterial growth after overnight incubation. For the definite determination of MIC, CellTiter-Blue® Cell Viability Assay (Promega, USA) was used (as above). The MIC was defined as the lowest compound concentration that prevented the color change of the Cell Viability solution (absence of bacterial growth; thus, suspension remained blue in color). For the definite determination of MIC, CellTiter-Blue® Cell Viability Assay (Promega, USA) was used (as above). To each well of the 96-well microplate, 20 μL of the Cell Viability Assay solution was added to the overnight (20 hours culture) and incubated at 37° C. for 4 hours. After the end of the incubation, pink and blue colors were used to differentiate viable from dead bacterial suspensions, respectively. The MIC was defined as the lowest compound concentration that prevented the color change.

To confirm bacterial death in response to the test compound and to determine the minimum bactericidal concentration (MBC), 50 μL of bacterial suspension in the well representing MIC and wells with X2 MIC, X4 MIC, and X8 MIC were spread on the surface of Mueller-Hinton agar plates and incubated at 37° C. for 24 hours. MBC was defined as the lowest concentration of the test compound that needed to kill≥99.9% of the microorganism. Thus, the lowest concentration showing no growth on the agar plate was considered as the MBC. To determine whether a test compound is bactericidal or bacteriostatic, MBC/MIC ratio was calculated. Antimicrobials are usually regarded as bactericidal if the MBC/MIC ratio is ≤4 and bacteriostatic if >4.

Time-kill study: Compound 1o was tested for the time required to kill the bacterial strain MRSA-1. A time-kill assay was performed by the broth micro-dilution method in accordance with the CLSI guidelines. Inoculum suspensions with approximately $5 \times 10^5$ CFU/mL of exponentially growing bacterial cells were incubated in each well of a 96-well plate. Two-fold serial dilutions of the test compound were added to each well at concentration ranged between X¼ MIC (0.78 μg/mL) to X32 MIC (100 μg/mL). Aliquots of 20 μL were removed from the inoculum culture after timed intervals of incubation (i.e. 0, 30 minutes, 1, 2, 4, 6, 8, and 24 hours), and serial 10-fold dilutions were prepared in 0.85% sodium chloride solution. Then, 10-100 μL of each dilution (as appropriate) were spread on the surface of Mueller-Hinton agar plates and incubated at 37° C. for 24 hours. Plate count technique was used to determine the number of viable cells for each time point. The experiments were performed in triplicate. Meropenem and ciprofloxacin were used as quality control antibiotics.

Examination of Bacterial Cell Walls by Atomic Force Microscope (AFM):

Compound 1o was tested against the bacterial strain MRSA-1. Exponentially growing bacterial cells were prepared in Mueller-Hinton broth at a concentration of approximately $10^8$ CFU/mL by adjusting the turbidity to 0.5 with a McFarland™ densitometer (DEN-1B, Grant-Bio, UK). Three tubes with a volume of 4 mL of the bacterial suspension were prepared: one tube served as a negative control (growth control) containing the bacterial suspension without any treatment, one tube was used as a positive control with the antibiotic meropenem (a carbapenem which acts by inhibiting cell wall synthesis) at a final concentration of 40 μg/mL, and the third tube contained the test compound 1o at a final concentration of 25 μg/mL. The three tubes were incubated at 37° C. for 4 hours. Bacterial cells were harvested from 2 mL broth culture by centrifugation at 3,000×g for 5 minutes. Pelleted bacterial cells were washed with 1 mL of sterile molecular biology grade water (Sigma, US) twice, and then pelleted again by centrifugation at 3,000×g for 5 minutes. Pelleted bacterial cells were finally suspended in 50 μL molecular biology grade water. Then, a 5 μL of concentrated bacterial suspension was spread on the surface of clean glass slide coated with poly-L-lysine (Knittel-Glass, Germany) and allowed to dry in air for 15 minutes. The slide was washed with sterile water to remove unattached bacterial cells and allowed to dry for 15 minutes. The slides were examined by atomic force microscopy (Nano Science Nanosurf Easy Scan 2 Flex™ AFM, Switzerland). Height, amplitude, and phase images were simultaneously acquired using tapping mode in air. Large scans (50 μm by 50 μm) were performed on randomly chosen sections of the glass slides to check the morphology of the bacterial population. High-magnification images (both 10 μm by 10 μm and 5 μm by 5 μm) were then taken for visualizing the bacterial cell wall.

Cytotoxicity:

The effect of the compounds on the survival of normal human fibroblast cells (F180) at different concentrations (5 and 2 μM) was tested by sulforhodamine B (SRB) assay. The anticancer drug doxorubicin was used as positive control and cells treated with DMSO served as a negative control. The antibiotics ciprofloxacin, amikacin, and meropenem were also included in the assay as controls. The surviving fraction of each compound was then calculated in reference to the negative control (DMSO).

What is claimed is:
1. A compound having the following formula:

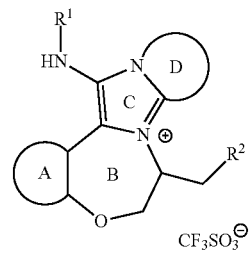

wherein:

is a phenyl ring which may be unsubstituted or substituted with 1, 2, 3, or 4 substituents independently selected from the group consisting of: a halogen atom, CN, $R^3$, $OR^3$, $SR^3$, $N(R^3)_2$, $C(O)R^3$, $C(O)OR^3$, $NR^3C(O)R^3$, $C(O)NR^3$, $SO_2R^3$, $NR^3SO_2R^3$, and $SO_2N(R^3)_2$;

$R^1$ is hydrogen or an unsubstituted or substituted alkyl, aryl, or heteroaryl group;

$R^2$ is selected from the group consisting of: $C(O)OR^3$, CN, $N(R^3)_2$, $C(O)R^3$, $C(O)NR^3$, $SO_2R^3$, $SO_2N(R^3)_2$, and $PO_2R^3$; and

is a 5 or 6 membered aryl or heteroaryl ring that is either unsubstituted or substituted with 1, 2, 3, or 4 substituents independently selected from the group consisting of: a halogen atom, CN, $R^3$, $OR^3$, $SR^3$, $N(R^3)_2$, $C(O)R^3$, $C(O)OR^3$, $NR^3C(O)R^3$, $C(O)NR^3$, $SO_2R^3$, $NR^3SO_2R^3$, and $SO_2N(R^3)_2$, $R^3$ is hydrogen or a substituted group selected from the group consisting of: a $C_{1-6}$ aliphatic group; a monocyclic 3-8 membered saturated, partially unsaturated, or aryl ring having 0-4 heteroatoms independently selected from nitrogen, oxygen, or sulfur; a bicyclic 8-10 membered saturated, partially unsaturated, or aryl ring having 0-5 heteroatoms independently selected from nitrogen, oxygen, or sulfur;

or a pharmaceutically acceptable salt thereof.

2. The compound of claim 1, wherein $R^3$ is selected from the group consisting of: —$CX_3$, —$CHX_2$, and —$CH_2X$, wherein X is chlorine, fluorine, bromine, or iodine.

3. The compound of claim 1, wherein ring D is pyrazine, quinolone, thiazole, or benzothiazole.

4. A process for the preparation of the compound of claim 1, the process utilizing a compound of formula I, a compound of formula II, and a compound of formula III as starting materials, wherein:

formula I is:

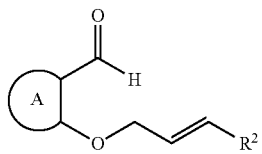

formula II is:

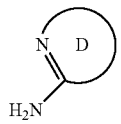

and formula III is:

is a phenyl ring which may be unsubstituted or substituted with 1, 2, 3, or 4 substituents independently selected from the group consisting of: a halogen atom, CN, $R^3$, $OR^3$, $SR^3$, $N(R^3)_2$, $C(O)R^3$, $C(O)OR^3$, $NR^3C(O)R^3$, $C(O)NR^3$, $SO_2R^3$, $NR^3SO_{2R}{}^3$, and $SO_2N(R^3)_2$;

is a 5 or 6 membered aryl or heteroaryl ring that is either unsubstituted or substituted with 1, 2, 3, or 4 substituents independently selected from the group consisting of: a halogen atom, CN, $R^3$, $OR^3$, $SR^3$, $N(R^3)_2$, $C(O)R^3$, $C(O)OR^3$, $NR^3C(O)R^3$, $C(O)NR^3$, $SO_2R^3$, $NR^3SO_2R^3$, and $SO_2N(R^3)_2$;

$R^1$ is hydrogen or an unsubstituted or substituted alkyl, aryl, or heteroaryl group; and $R^2$ is selected from the group consisting of: $C(O)OR^3$, CN, $N(R^3)_2$, $C(O)R^3$, $C(O)NR^3$, $SO_2R^3$, $SO_2N(R^3)_2$, and $PO_2R^3$;

$R^3$ is hydrogen or a substituted group selected from the group consisting of: a $C_{1-6}$ aliphatic group; a monocyclic 3-8 membered saturated, partially unsaturated, or aryl ring having 0-4 heteroatoms independently selected from nitrogen, oxygen, or sulfur; a bicyclic 8-10 membered saturated, partially unsaturated, or aryl ring having 0-5 heteroatoms independently selected from nitrogen, oxygen, or sulfur;

the process comprising:

(a) forming a first reaction mixture from ingredients comprising the compound of formula I, the compound of formula II, a solvent, and a first metal triflate;

(b) adding the compound of formula III to the first reaction mixture, to form a second reaction mixture;

(c) adding a second metal triflate to the second reaction mixture, to form a product compound according to claim 1.

5. The process of claim 4, wherein the solvent is methanol, ethanol, or acetonitrile.

6. The process of claim 4, wherein the first metal triflate and second metal triflate are independently selected from the group consisting of scandium triflate, ytterbium triflate, and combinations thereof.

7. The compound according to claim 1, selected from one of the following chemical structures, including enantiomers and diastereoisomers thereof:

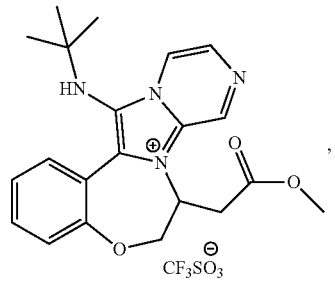

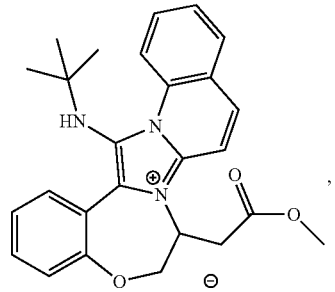

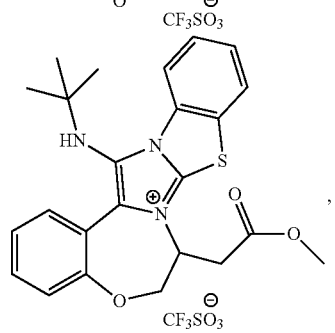

37
-continued
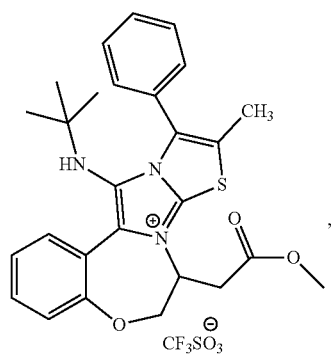
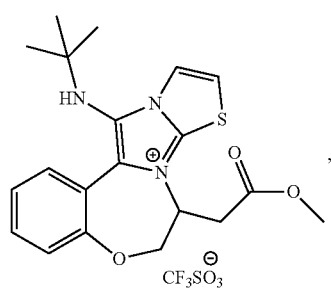
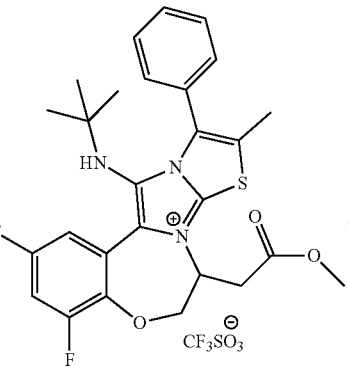
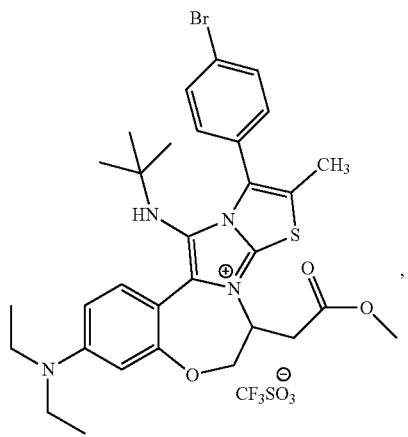
38
-continued
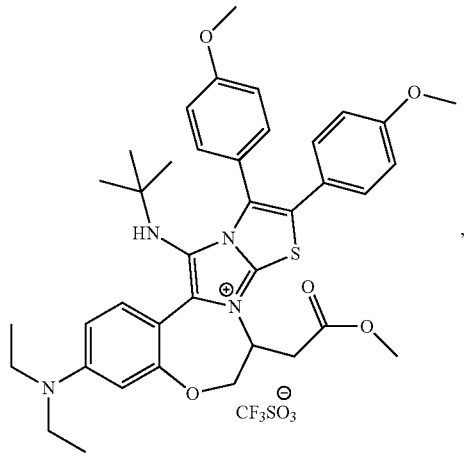
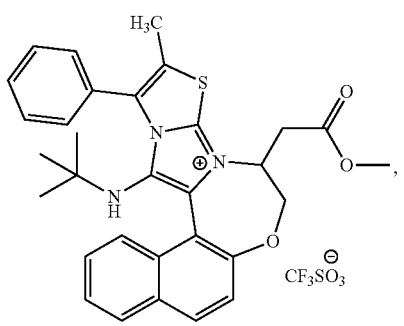
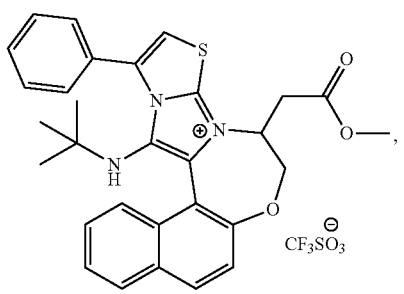
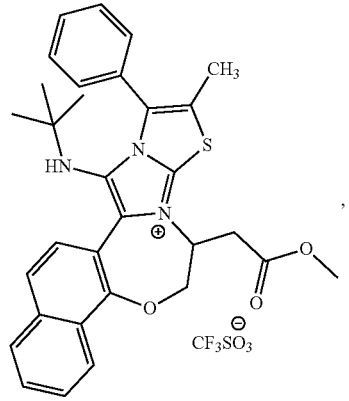

-continued
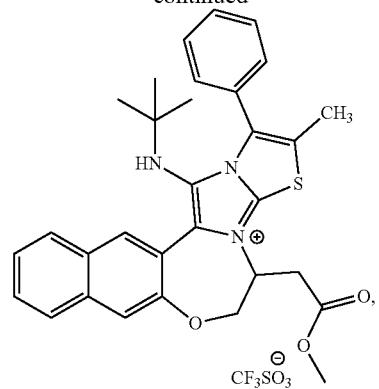
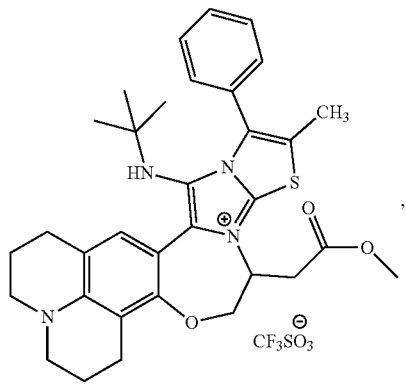
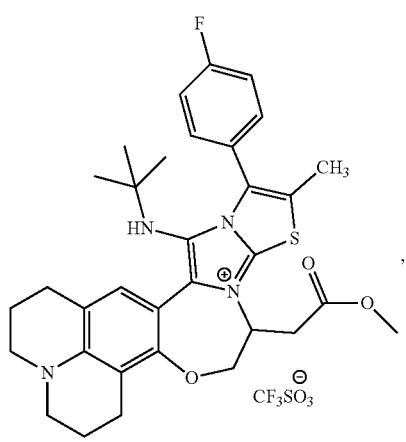
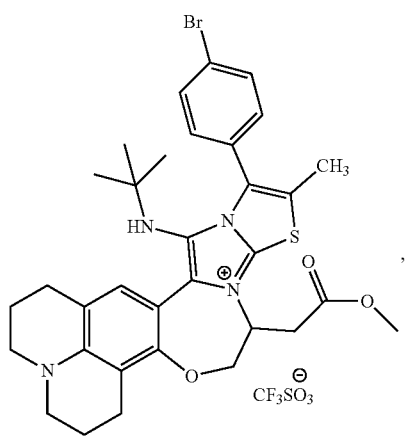
-continued
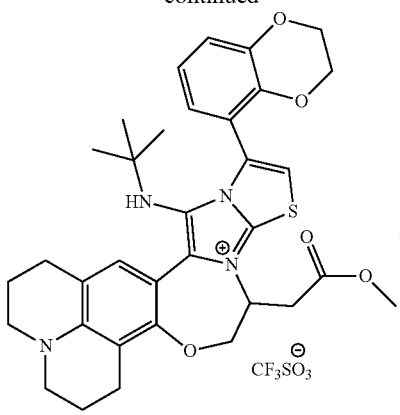
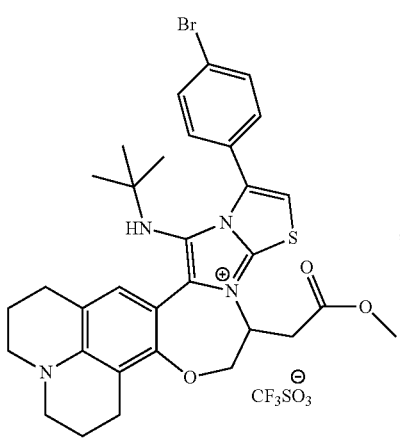
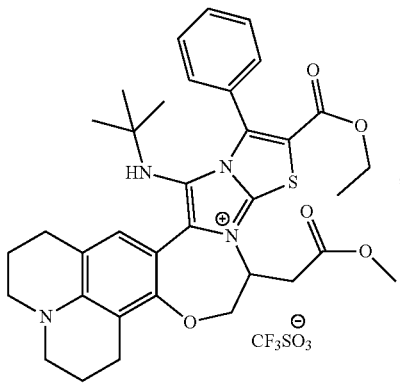
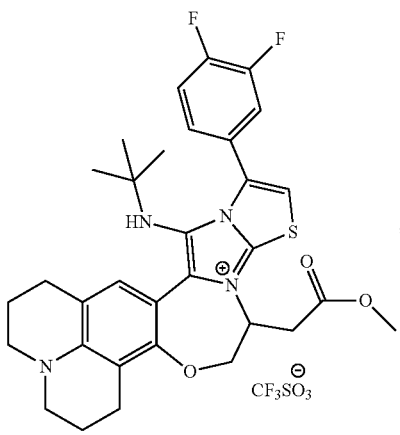

41
-continued
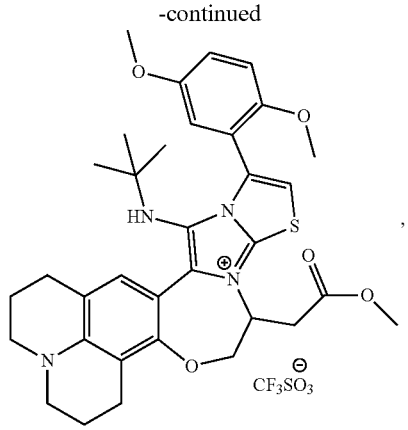
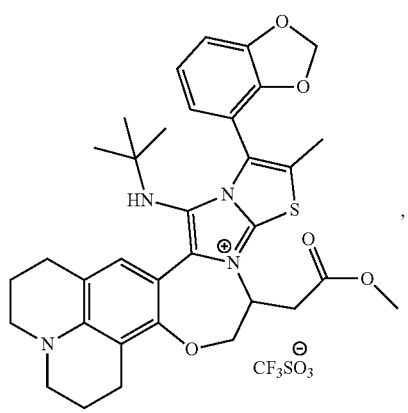
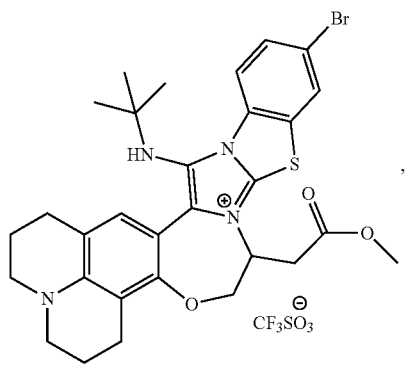
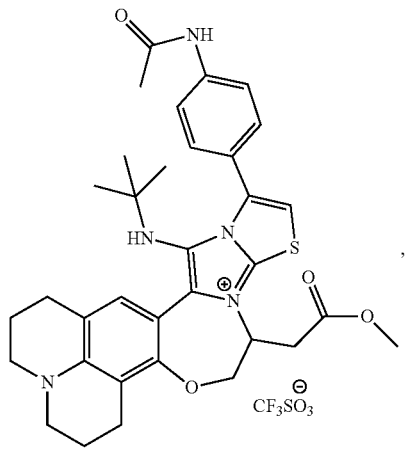
42
-continued
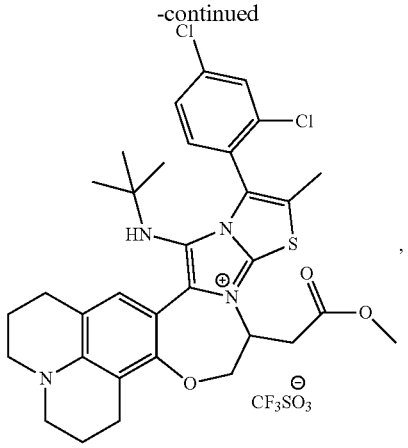
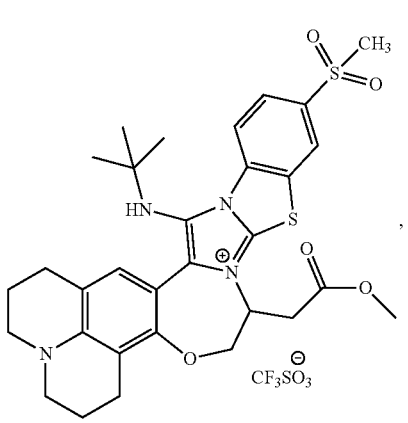
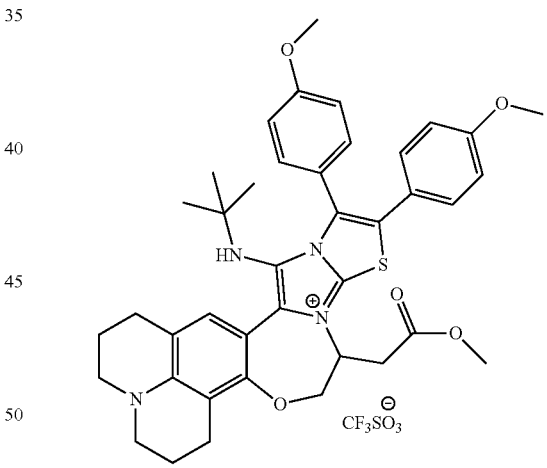
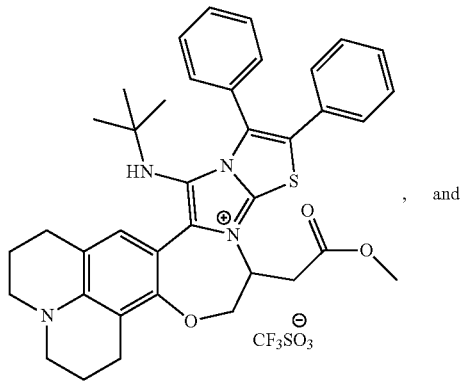, and -continued

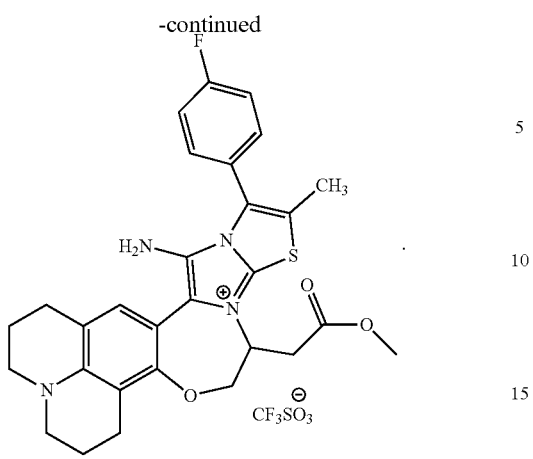

8. A pharmaceutical composition comprising one or more compounds of claim 7 as an active ingredient.

9. The process of claim 4, wherein an imine compound of formula IV is formed in the first mixture.

10. The process of claim 4, further comprising purifying the product compound by column chromatography or recrystallization.

11. The process of claim 10, wherein mobile phase for the column chromatography is selected from the group consisting of MeOH/DCM and EtoAc/hexane.

12. A pharmaceutical composition comprising one or more compounds of claim 1.

* * * * *

UNITED STATES PATENT AND TRADEMARK OFFICE
CERTIFICATE OF CORRECTION

PATENT NO. : 10,526,343 B2
APPLICATION NO. : 15/935120
DATED : January 7, 2020
INVENTOR(S) : Altel et al.

Page 1 of 1

It is certified that error appears in the above-identified patent and that said Letters Patent is hereby corrected as shown below:

In the Claims

Column 35, Claim 4, Line 55, after "$NR^3SO_{2R}{}^3$", should be --$NR^3SO_2R^3$--.

Signed and Sealed this
Twenty-fifth Day of February, 2020

Andrei Iancu
*Director of the United States Patent and Trademark Office*